(12) United States Patent
Wakita et al.

(10) Patent No.: US 9,488,631 B2
(45) Date of Patent: *Nov. 8, 2016

(54) PRESERVATION ENVIRONMENT INFORMATION OUTPUT METHOD, PRESERVATION ENVIRONMENT INFORMATION OUTPUT DEVICE, AND RECORDING MEDIUM

(71) Applicant: Panasonic Intellectual Property Management Co., Ltd., Osaka (JP)

(72) Inventors: Yumi Wakita, Nara (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 80 days.

This patent is subject to a terminal disclaimer.

(21) Appl. No.: 14/656,512

(22) Filed: Mar. 12, 2015

(65) Prior Publication Data
US 2015/0268211 A1 Sep. 24, 2015

(30) Foreign Application Priority Data

Mar. 18, 2014 (JP) .................................. 2014-055417

(51) Int. Cl.
G01N 33/12 (2006.01)
G01N 21/47 (2006.01)

(52) U.S. Cl.
CPC .......... G01N 33/12 (2013.01); G01N 21/4738 (2013.01)

(58) Field of Classification Search
CPC ...... G01N 33/12; G01N 33/02; G01N 21/33; G01N 21/55
See application file for complete search history.

(56) References Cited

U.S. PATENT DOCUMENTS 4,650,752 A * 3/1987 Ohashi et al. .................. 435/15

FOREIGN PATENT DOCUMENTS

| JP | 6-109699 | | 4/1994 |
|---|---|---|---|
| JP | 07213488 | A * | 8/1995 |
| JP | 2007-292512 | | 11/2007 |

* cited by examiner

*Primary Examiner* — Marcus Taningco
(74) *Attorney, Agent, or Firm* — Wenderoth, Lind & Ponack, L.L.P.

(57) ABSTRACT

A method of determining preservation environment information includes irradiating left and right eyes of a fish with ultraviolet rays, taking ultraviolet images of the fish eyes by one or more ultraviolet cameras, analyzing the ultraviolet images by a computer, determining preservation environment of the fish based on luminance of each of iris portions in the left and right fish eyes, and outputting information representing a determination result to a display.

11 Claims, 27 Drawing Sheets

FIG. 6
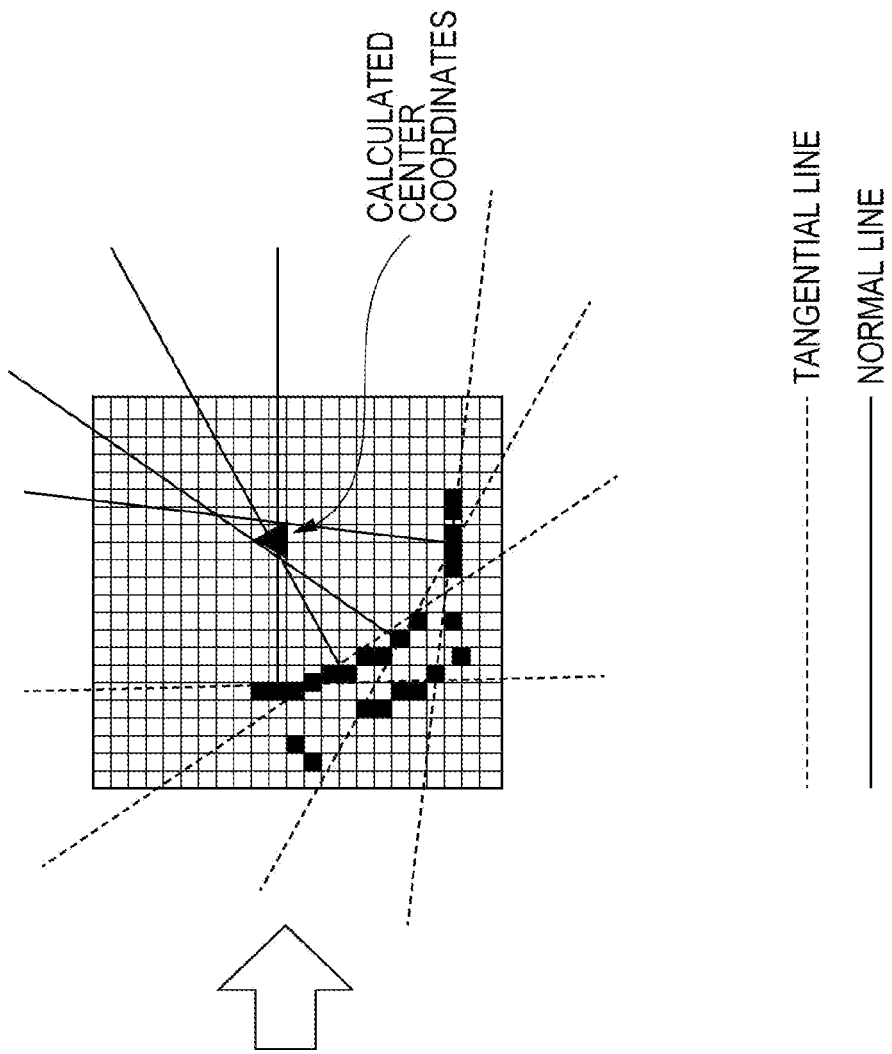
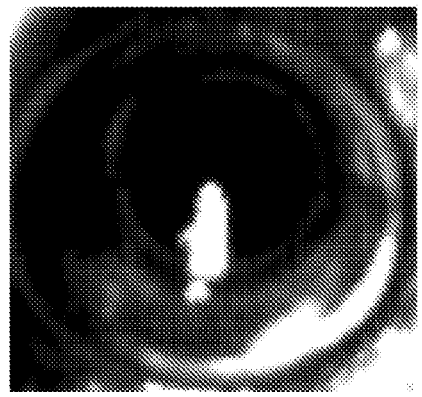

FIG. 12

| BILATERAL DIFFERENCE IN FRESHNESS INDEX VALUE (LEFT − RIGHT) | INFORMATION INDICATING PRESERVATION ENVIRONMENT OF FISH |
|---|---|
| NOT MORE THAN −A1 (e.g., −100) | FISH HAS NOT BEEN PRESERVED UNDER SUBSTANTIALLY SAME CONDITIONS AT LEFT AND RIGHT SIDES (PRESERVED UNDER BAD CONDITIONS AT RIGHT SIDE) |
| LARGER THAN −A1 AND SMALLER THAN A1 | FISH HAS BEEN PRESERVED UNDER SUBSTANTIALLY SAME CONDITIONS AT LEFT AND RIGHT SIDES |
| NOT LESS THAN A1 (e.g., 100) | FISH HAS NOT BEEN PRESERVED UNDER SUBSTANTIALLY SAME CONDITIONS AT LEFT AND RIGHT SIDES (PRESERVED UNDER BAD CONDITIONS AT LEFT SIDE) |

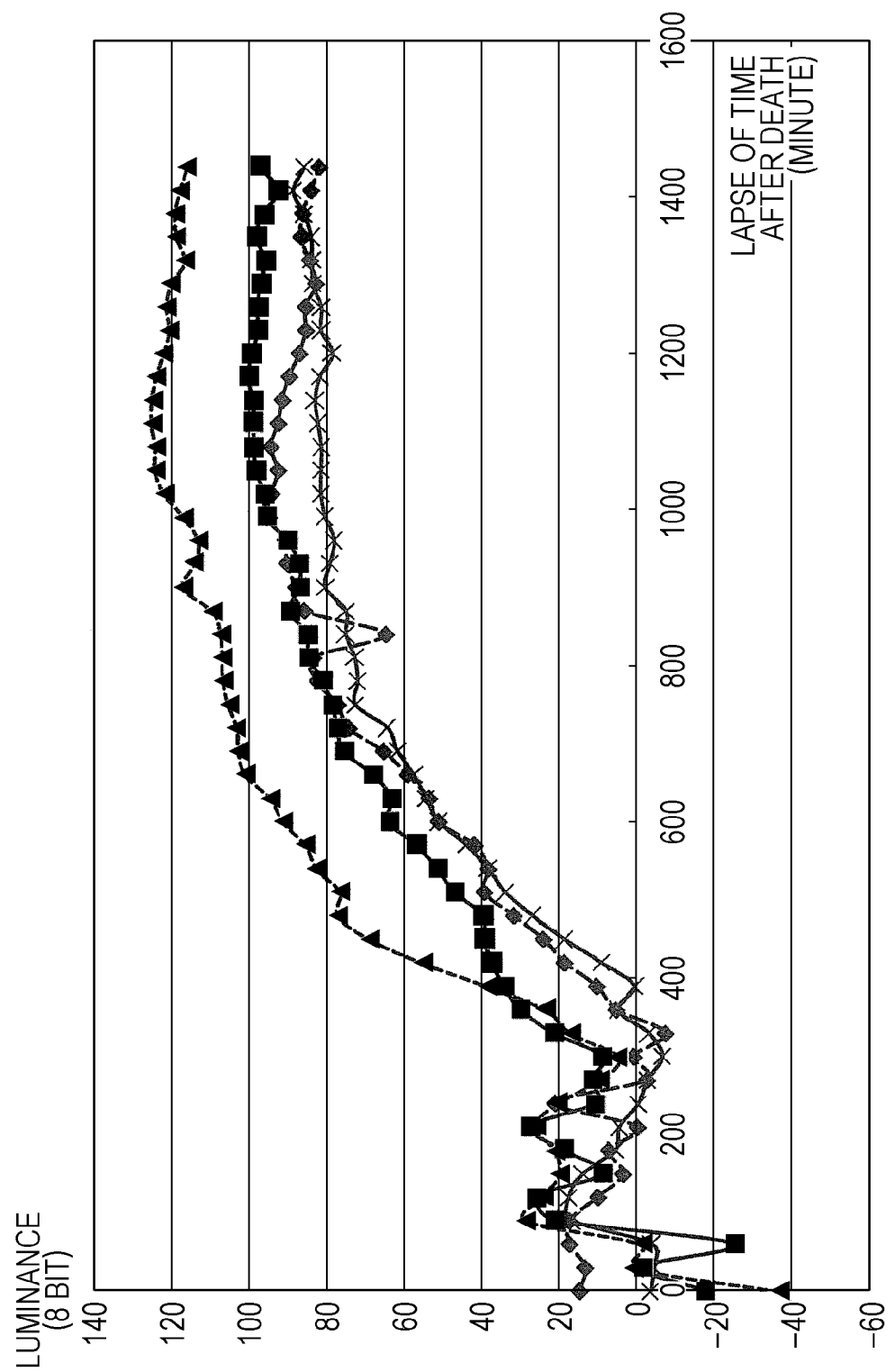

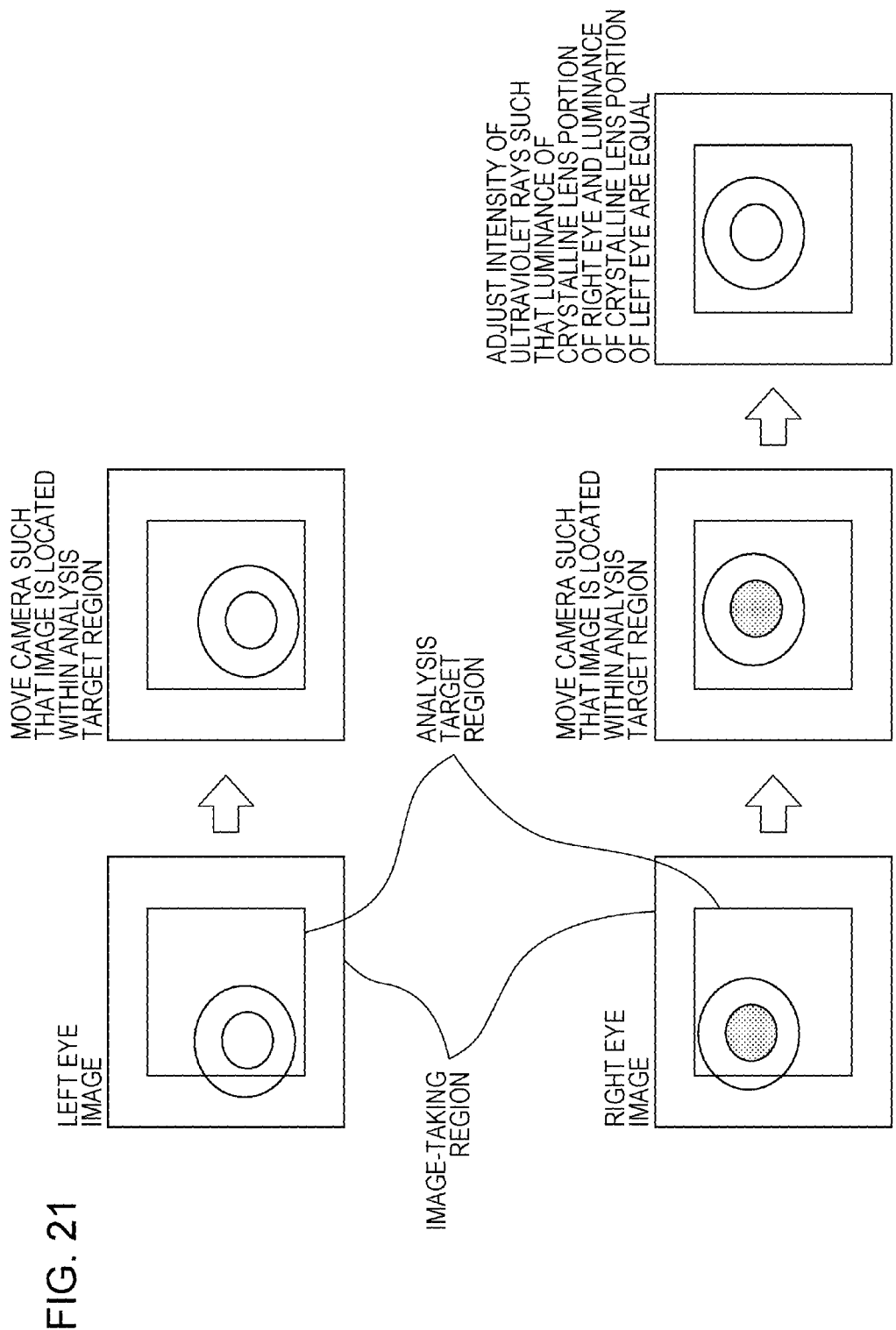

FIG. 23

| BILATERAL DIFFERENCE IN AVERAGE LUMINANCE VALUE OF IRIS (LEFT – RIGHT) | INFORMATION INDICATING PRESERVATION ENVIRONMENT OF FISH |
|---|---|
| NOT MORE THAN −100 | FISH HAS BEEN PRESERVED UNDER WORSE CONDITIONS AT RIGHT SIDE THAN AT LEFT SIDE |
| LARGER THAN −100 AND SMALLER THAN 100 | FISH HAS BEEN PRESERVED UNDER SUBSTANTIALLY SAME CONDITIONS AT LEFT AND RIGHT SIDES |
| NOT LESS THAN 100 | FISH HAS BEEN PRESERVED UNDER WORSE CONDITIONS AT LEFT SIDE THAN AT RIGHT SIDE |

PRESERVATION ENVIRONMENT INFORMATION OUTPUT METHOD, PRESERVATION ENVIRONMENT INFORMATION OUTPUT DEVICE, AND RECORDING MEDIUM

BACKGROUND

1. Technical Field

The present disclosure relates to a preservation environment information output method, a preservation environment information output device, and a recording medium, which are used to output preservation environment information of fish.

2. Description of the Related Art

From the viewpoint of keeping quality of fresh fish (fish for foods), the fish is demanded to be preserved in proper preservation environment immediately after being caught. Fresh fish is generally preserved in a cooler box, a refrigerator, and so on. In such a preservation method, freshness of the preserved fish differs depending on differences in the preservation environment, e.g., imbalance of temperature inside the cooler box or the refrigerator, and temperature differences among contact surfaces of fish bodies.

Under such a situation, a technique for evaluating the state of preserved fish is demanded to evaluate, e.g., propriety of preservation environment of the fish and to improve the preservation environment, for example. In this regards, there is known a technique of evaluating a preservation state of fish, shellfish, etc. by measuring bioelectricity (see Japanese Unexamined Patent Application Publication No. 6-109699).

SUMMARY

However, fresh fish is mostly delivered to fields of distribution and consumption in a dead state through treatment, such as depletion of blood from the fish, after being caught, and the dead fish does not generate bioelectricity. Accordingly, the technique disclosed in Japanese Unexamined Patent Application Publication No. 6-109699 is not adapted for evaluating the preservation state of the fresh fish.

One non-limiting and exemplary embodiment provides a preservation environment information output method of outputting preservation environment information of fish without employing bioelectricity. Here, the term "preservation environment of fish" is used as a word including environments that affect the preservation state, such as facilities, methods, temperature, humidity, and forms related to the preservation of fish.

In one general aspect, the techniques disclosed here feature a preservation environment information output method that includes obtaining first information indicating luminance of an iris portion of a left eye of a fish, the left eye being irradiated with first ultraviolet rays, and second information indicating luminance of an iris portion in a right eye of the fish, the right eye being irradiated with second ultraviolet rays, and outputting environment information representing preservation environment of the fish based on the first information and the second information.

The preservation environment information output method according to the present disclosure is able to output preservation environment information of fish without employing bioelectricity, and is effective in, for example, evaluating propriety of preservation environment of fresh fish.

It should be noted that general or specific embodiments may be implemented as a device, a system, an integrated circuit, a computer program, a storage medium such as a computer-readable CD-ROM, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 illustrates a manner of calculating a center of the fish eye;

FIG. 12 is a table representing a bilateral difference in a freshness index value and information indicating preservation environment in a linked manner;

FIG. 19 is a graph plotting time-lapsed changes in differences of average luminance values of iris portions of plural fishes between ultraviolet images and infrared images;

FIG. 21 is an illustration to explain adjustment of the ultraviolet camera;

FIG. 23 is a table representing a bilateral difference in an average luminance value of the iris portion and information indicating preservation environment in a linked manner;

DETAILED DESCRIPTION

Figure 1:
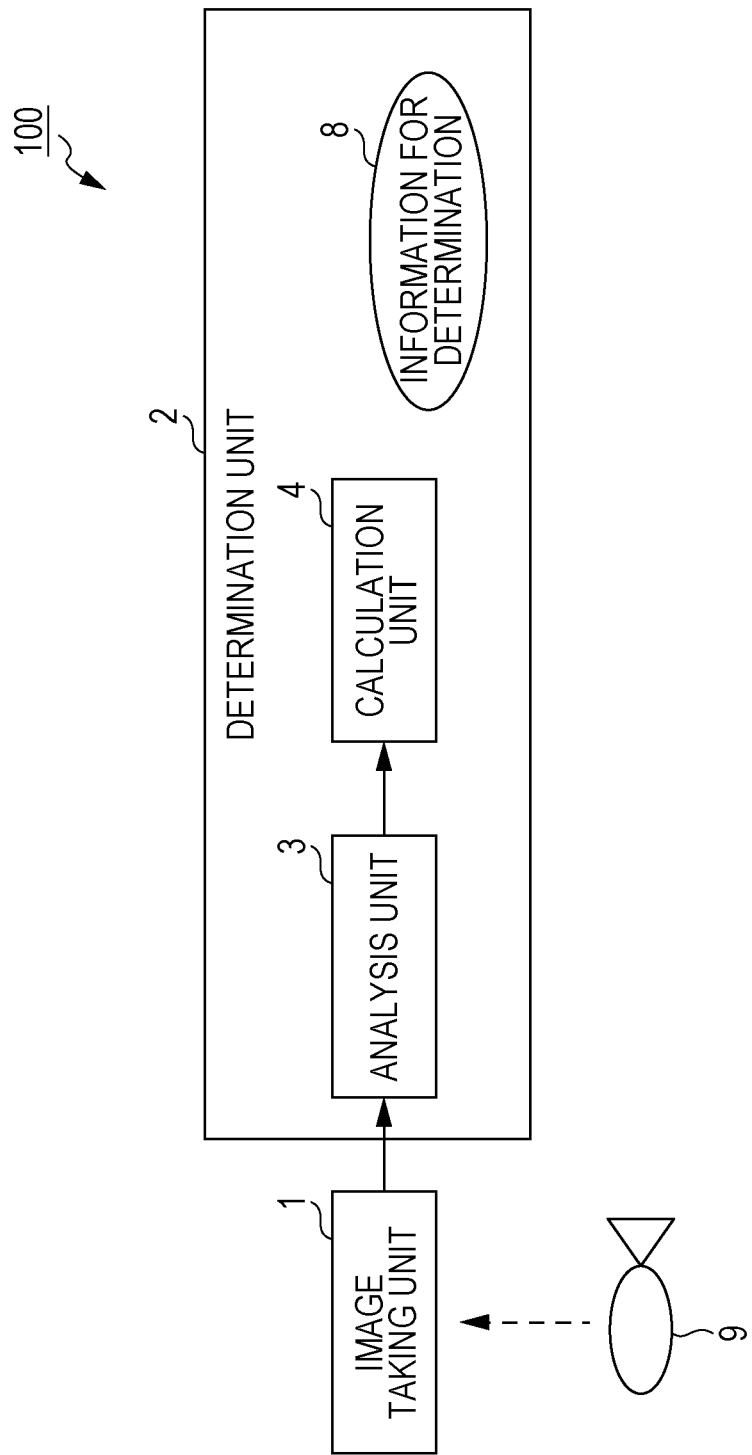
FIG. 1 is a functional block diagram of a preservation environment information output device according to a first embodiment.

Aiming to output preservation state information of a fish without resorting to bioelectricity, a preservation environment information output method according to the present disclosure includes obtaining first information indicating luminance of an iris portion of a left eye of a fish, the left eye being irradiated with first ultraviolet rays, and second information indicating luminance of an iris portion of a right eye of the fish, the right eye being irradiated with second ultraviolet rays, and outputting environment information representing preservation environment of the fish based on the first information and the second information. The preservation environment information output method enables preservation environment of fish to be determined properly. Since the preservation environment of the fish is determined by irradiating fish eyes with ultraviolet rays and measuring luminance of each of the fish eyes (e.g., through taking an image of each fish eye), the method can be practiced in a manner not invasive to the fish.

The preservation environment information output method may further include taking a first ultraviolet image containing an ultraviolet image of the left eye irradiated with the first ultraviolet rays and a second ultraviolet image containing an ultraviolet image of the right eye irradiated with the second ultraviolet rays, wherein the outputting may include determining the environment information, and outputting the environment information, and wherein the first information may be extracted from the first ultraviolet image, and the second information may be extracted from the second ultraviolet image. With those features, since the preservation environment of the fish can be determined through an image analysis, it is possible to make the determination in a comparatively quick way.

The preservation environment information output method may further include obtaining third information indicating luminance of a crystalline lens portion of the left eye, which is irradiated with the first ultraviolet rays, from the first ultraviolet image, and fourth information indicating luminance of a crystalline lens portion of the right eye, which is irradiated with the second ultraviolet rays, from the second ultraviolet image, wherein the determination of the environment information may be performed by comparing a first freshness index value, which is obtained by normalizing the first information by employing the third information, with a second freshness index value, which is obtained by normalizing the second information by employing the fourth information. With those features, the preservation environment of the fish can be determined while influences of individual differences among fishes, differences in image taking conditions, etc. are held less.

The preservation environment information output method may further include taking a first infrared image containing an infrared image of the left eye irradiated with first infrared rays and a second infrared image containing an infrared image of the right eye irradiated with second infrared rays, and obtaining fifth information indicating luminance of the iris portion of the left eye, which is irradiated with the first infrared rays, from the first infrared image, and sixth information indicating luminance of the iris portion of the right eye, which is irradiated with the second infrared rays, from the second infrared image, wherein the determination of the environment information may be performed by comparing a third freshness index value, which is obtained by normalizing the first information by employing the fifth information, with a fourth freshness index value, which is obtained by normalizing the second information by employing the sixth information. With those features, as in the above-described case, the preservation environment of the fish can be determined while influences of individual differences among fishes, differences in image taking conditions, etc. are held less.

When a discrepancy between the first freshness index value and the second freshness index value is smaller than a specific value, information indicating that temperatures at left and right sides of the fish have been held substantially at same may be output as the environment information, and when the discrepancy is not smaller than the specific value, information indicating that the temperatures at the left and right sides of the fish have not been held substantially at same may be output as the environment information. Here, the range where temperatures are substantially at same implies a range where temperatures can be regarded as being equal in practical point of view (namely, it is allowed to regard temperatures as being the same), e.g., a range within ±5 degrees from a certain temperature. As a result, users can confirm for the preservation environment of the fish whether the temperatures at the left and right sides of a fish body have been held substantially equal.

On that occasion, the environment information may be output with inclusion of information indicating, based on the first information and the second information, whether the fish has been refrigerated at the left and right sides thereof. With that feature, users can confirm for the preservation environment of the fish whether the fish has been held in refrigerated environment.

When a discrepancy between the third freshness index value and the fourth freshness index value is smaller than a specific value, information indicating that temperatures at left and right sides of the fish have been held substantially at same may be output as the environment information, and when the discrepancy is not smaller than the specific value, information indicating that the temperatures at the left and right sides of the fish have not been held substantially at same may be output as the environment information. Here, the range where temperatures are substantially at same implies a range where temperatures can be regarded as being equal in practical point of view (namely, it is allowed to regard temperatures as being the same), e.g., a range within ±5 degrees from a certain temperature. As a result, users can confirm for the preservation environment of the fish whether the temperatures at the left and right sides of a fish body have been held substantially equal.

On that occasion, the environment information may be output with inclusion of information indicating, based on the first information and the second information, whether the fish has been refrigerated at the left and right sides thereof. With that feature, users can confirm for the preservation environment of the fish whether the fish has been held in refrigerated environment.

The preservation environment information output method may further include obtaining third information indicating luminance of a crystalline lens portion of the left eye, which is irradiated with the first ultraviolet rays, from the first ultraviolet image, and fourth information indicating luminance of the crystalline lens portion of the right eye, which is irradiated with the second ultraviolet rays, from the second ultraviolet image, and when a discrepancy between the third information and the fourth information is not less than a specific value, the first ultraviolet image and the second ultraviolet image are taken again after adjusting one or both of intensities of the first ultraviolet rays and the second ultraviolet rays. With that feature, the preservation environment of the fish can be determined in accordance with a bilateral difference in luminance of the iris portions between the left and right fish eyes while influences of differences between the left and right fish eyes themselves, differences in image taking conditions between the left and right sides, etc. are held less.

A preservation environment information output device according to the present disclosure includes an acquisition unit that obtains first information indicating luminance of an iris portion of a left eye of a fish, the left eye being irradiated with first ultraviolet rays, and second information indicating luminance of an iris portion of a right eye of the fish, the right eye being irradiated with second ultraviolet rays, and an output unit that outputs environment information representing preservation environment of the fish based on the first information and the second information. Since the information indicating the luminance of the iris portion can be obtained in a short time in a manner not invasive to fish, users of the device can quickly confirm the preservation environment of the fish without degrading quality of the fish.

It should be noted that general or specific embodiments involve one or combinations of plural ones selected from a device, a system, a method, an integrated circuit, a computer program, and a computer-readable recording medium.

Embodiments will be described below with reference to the drawings. It is to be noted that any of the following embodiments represents one specific example of the present disclosure. Thus, numerical values, shapes, materials, components, arrangements and connected forms of the components, steps, sequences of steps, and so on, which are described in the following embodiments, are merely illustrative, and they are not purported to limit the present disclosure. Among the components in the following embodiments, those ones other than the components not stated in independent claims, which define most significant concepts, are components that can be optionally added. Moreover, the drawings are schematic views and they are not always illustrated in an exact sense.

In the following embodiments, particularly, a preservation environment information output device is described as one form implementing a preservation environment information output method that analyzes ultraviolet images of left and right eyes of a fish, and that determines preservation environment of the fish based on a difference in luminance between the left and right fish eyes.

First Embodiment

A preservation environment information output device 100 according to a first embodiment of the present disclosure will be described below with reference to the drawings.
(Configuration)

FIG. 1 is a functional block diagram of the preservation environment information output device 100 according to the first embodiment. As illustrated in FIG. 1, the preservation environment information output device 100 includes an image taking unit 1 and a determination unit 2 as functional components.

Here, the image taking unit 1 has the function of photographing a fish (sample) 9 from the left side and the right side of a fish body, and generating images including fish eyes (a left-side image is called a "left eye image" and a right-side image is called a "right eye image" hereinafter). The determination unit 2 has the function of determining preservation environment of the fish 9 based on the left eye image and the right eye image, which have been generated by the image taking unit 1, and outputting a determination result. The determination unit 2 includes an analysis unit 3 that extracts, from the left eye image and the right eye image, image data corresponding to each of an iris portion and a crystalline lens portion of the fish eye, and a calculation unit 4 that calculates, from the extracted image data, a specific index value (referred to as a "freshness index value A" hereinafter) for each of the left side and the right side of the fish body. The determination unit 2 further accumulates information 8 for determination, which is used to determine the preservation environment of the fish depending on the freshness index value A for each of the left side and the right side.

Figure 2:
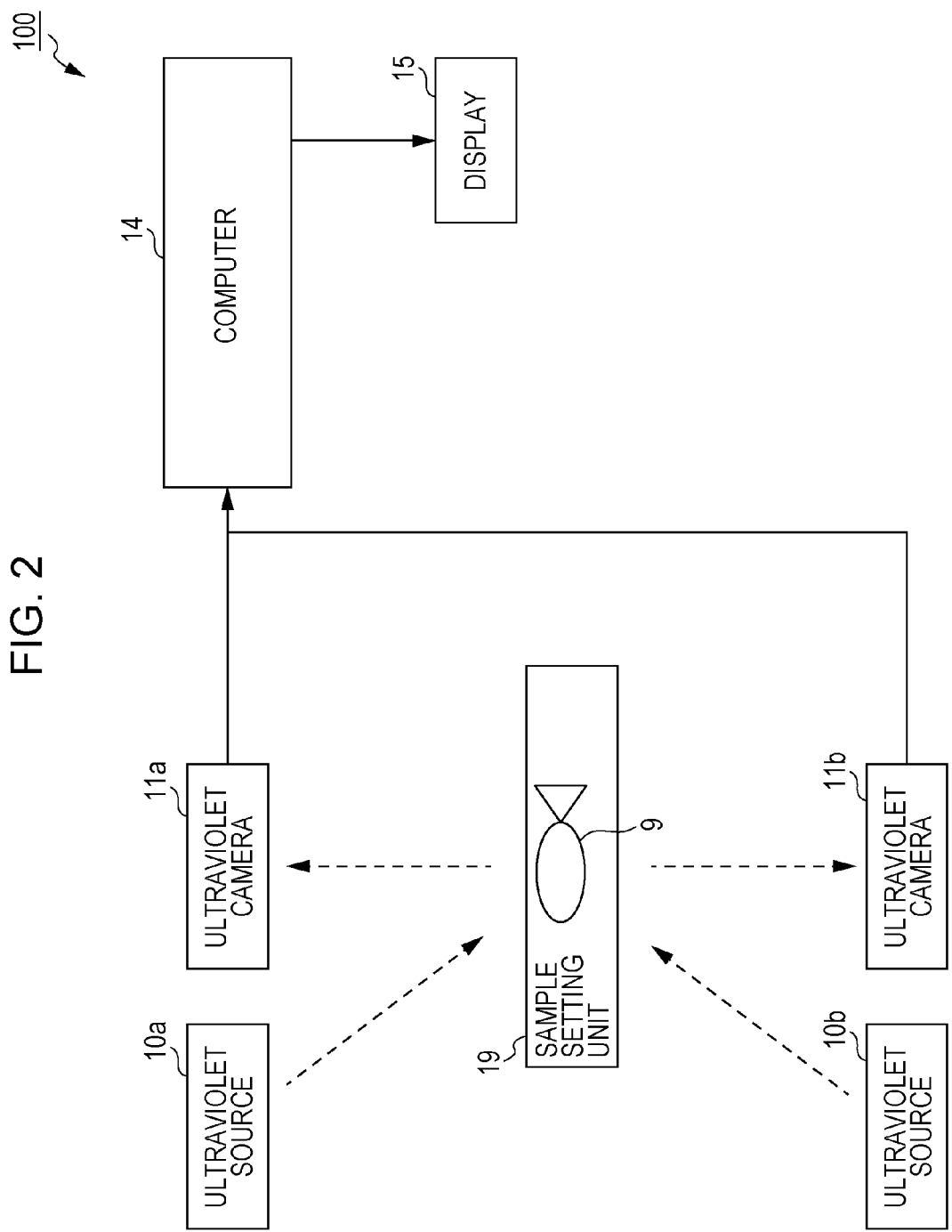
FIG. 2 is a hardware configuration diagram of the preservation environment information output device according to the first embodiment.

FIG. 2 is a hardware configuration diagram of the preservation environment information output device 100 according to the first embodiment.

As illustrated in FIG. 2, the preservation environment information output device 100 includes ultraviolet sources 10a and 10b, ultraviolet cameras 11a and 11b, a sample setting unit 19, a computer 14, and a display 15. Here, the computer 14 includes a memory, a processor, an input device, an interface for connection between relevant components, etc., and it functions as a device for implementing the function of the determination unit 2 with the processor executing a control program stored in the memory. The computer 14 may include an auxiliary storage device, such as a hard disk, in addition to the memory (main storage device).

Figure 3:
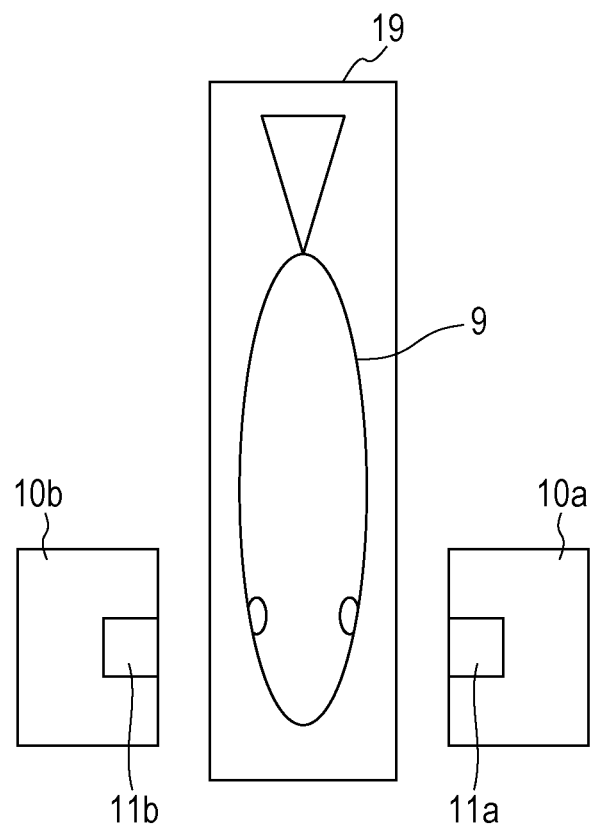
FIG. 3 is a schematic view to explain a sample setting unit in the preservation environment information output device.

The function of the image taking unit 1 is implemented by irradiating the fish 9, which is set on the sample setting unit 19, with ultraviolet rays emitted from the ultraviolet sources 10a and 10b, receiving the ultraviolet rays reflected from the fish 9 by the ultraviolet cameras 11a and 11b, and generating the left eye image and the right eye image. In more detail, the ultraviolet source 10a emits ultraviolet rays to the fish eye on the left side of the fish body, and the ultraviolet camera 11a receives the ultraviolet rays reflected from the left fish eye. The ultraviolet source 10b emits ultraviolet rays to the fish eye on the right side of the fish body, and the ultraviolet camera 11b receives the ultraviolet rays reflected from the right fish eye. The sample setting unit 19 is a member capable of setting the fish body in such a stable state as enabling images of the left and right fish eyes to be taken. The sample setting unit 19 is in the form of a box that does not have an upper cover, and that is made of a material transparent to light in an ultraviolet range, for example. A width of the box in the left-and-right direction is larger than the width of the fish, but smaller than the height of the fish. Left and right sidewalls of the box may be movable to approach each other to sandwich the fish body in the widthwise direction. The material transparent to the light in the ultraviolet range is, for example, a plate made of, e.g., quartz glass, calcium fluoride, or magnesium fluoride. As illustrated in FIG. 3, the sample setting unit 19 may be constituted such that the fish body is set upright from an upward direction with a backbone of the fish directed downwards vertically, and that the images of the fish eyes can be taken from both the left and right sides with the backbone of the fish body being at a center. Alternatively, the fish body may be set on the sample setting unit 19 to lie horizontally such that the left side or the right side of the fish body, which provides a comparatively flat surface in general fish, is directed downwards vertically, and that the images of the fish eyes can be taken from the lower side and the upper side in the vertical direction. The ultraviolet sources 10a and 10b and the ultraviolet cameras 11a and 11b are adapted for an ultraviolet range (e.g., a wavelength band of 300 nm to 400 nm), and are each fixedly or movably set at a position where the image of the left or right fish eye can be taken by the ultraviolet camera. To allow the images of the left and right fish eyes to be taken by the ultraviolet cameras 11a and 11b under as possible as equal conditions, respective distances from the sample setting unit 19 to the cameras and the light sources, field angles of the cameras, etc. are adjusted to be kept equal on both sides.

The function of the determination unit 2 is implemented by the computer 14 and the display 15. More specifically, the function of the determination unit 2 is implemented through the steps of obtaining both-side images, which have been taken by the ultraviolet cameras 11a and 11b, through, e.g., the interfaces for connection between relevant components, analyzing both the images to calculate the freshness index values A for the left and right sides, determining the preservation environment of the fish based on the calculated freshness index values A, and displaying a determination result on the display 15. The information 8 for determination, accumulated in the storage device, such as the memory of the computer 14, is used to determine the preservation environment of the fish. As processing to analyze both the images, the computer 14 executes processing to extract eye fish portions from both the images, processing to discriminate an iris portion and a crystalline lens portion of each fish eye, and processing to calculate average luminance values of the individual portions of the left and right fish eyes and to calculate the freshness index value A based on a difference between the calculated average luminance values for each fish eye. Moreover, the computer 14 executes, for example, processing to compare the freshness index values A for the left and right sides, and to determine the preservation environment based on a comparison result (discrepancy between the freshness index values A) by referring to the information 8 for determination. In other words, the preservation environment is determined by comparing index values for the left and right sides, each of which reflects luminance of the iris portion of the left or right fish eye, namely depending on a discrepancy (including, e.g., a difference or ratio between the left and right sides) between the index values for the left and right sides.

(Operation)

Figure 4:
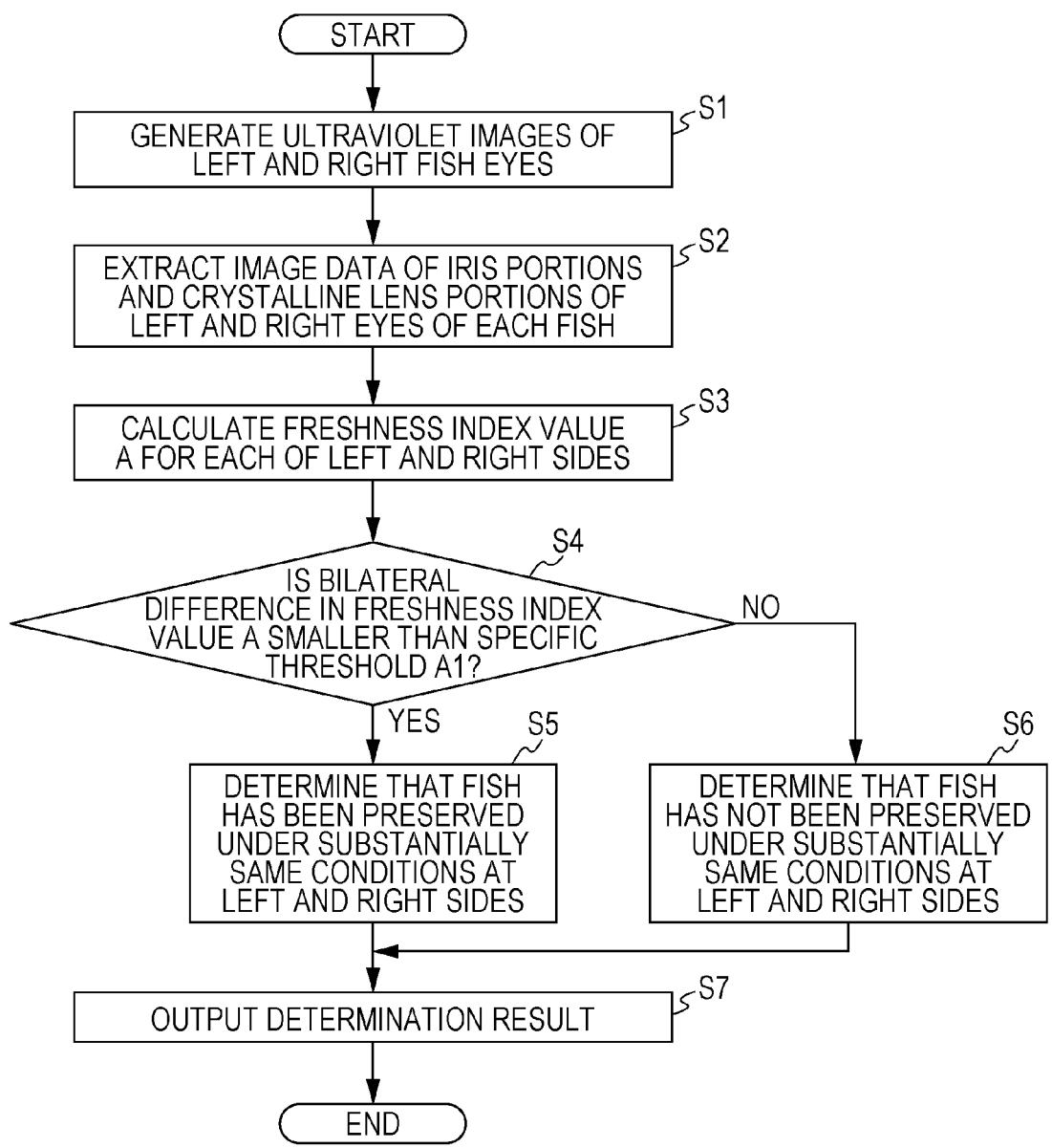
FIG. 4 is a flowchart representing the operation of the preservation environment information output device according to the first embodiment.

FIG. 4 is a flowchart representing the operation of the preservation environment information output device 100.

The operation of the preservation environment information output device 100 having the above-described configuration will be described below following the flowchart of FIG. 4 along with explanation of individual procedures while referring to FIGS. 5 to 12.

The description is made on an assumption that the fish 9 is in a state stably set on the sample setting unit 19.

First, the image taking unit 1 takes an image of the left fish eye by the ultraviolet camera 11a with the ultraviolet rays emitted from the ultraviolet source 10a, thereby generating the left eye image, and takes an image of the right fish eye by the ultraviolet camera 11b with the ultraviolet rays emitted from the ultraviolet source 10b, thereby generating the right eye image (processing step S1). The left eye image and the right eye image are taken at the same time, for example. The left eye image and the right eye image thus generated are each an assembly of image data (luminance values) at individual pixel positions that constitutes a two-dimensional space. The luminance value is expressed as 8-bit data (256 gradations), for example. In order to increase accuracy in determining the preservation state of the fish, it is effective to some extent to adjust, e.g., directions of optical axes of the ultraviolet cameras 11a and 11b, field angles thereof, and sizes of the generated images, namely to adjust image-taking conditions (setting) such that the images of the entire left and right fish eyes and peripheral portions thereof are taken with higher resolution.

Then, the determination unit 2 obtains the left eye image and the right eye image generated by the image taking unit 1, and the analysis unit 3 extracts image data of the iris portions and the crystalline lens portions of the fish eyes from the obtained images (processing step S2). While the image data of the iris portions and the crystalline lens portions may be extracted by desired one of suitable methods, those data may be extracted by the following method, for example.

Figure 5:
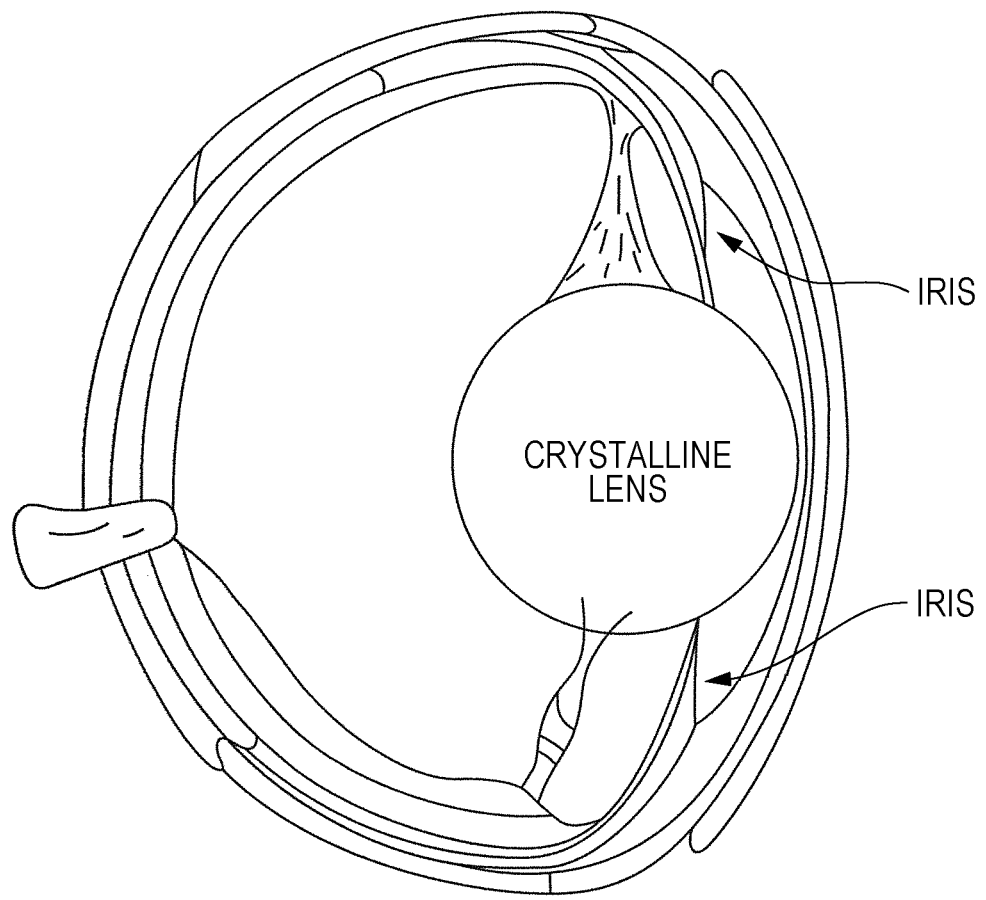
FIG. 5 is a sectional view illustrating positions of an iris and a crystalline lens in a fish eye.

A first derivation filter is applied to each image including the fish eye to obtain an image representing a portion where a spatial gradient of an image data value (luminance value) is steep (e.g., larger than a specific threshold), namely a region where contrast is greatly changed (so-called edge region). From the edge region, a region most analogous to a double-circle pattern (i.e. a location corresponding to the double-circle pattern), which represents a boundary line between a fish eye portion and a peripheral portion and a boundary line between the iris portion and the crystalline lens portion in the fish eye portion, is detected by pattern matching, for example. Based on the location corresponding to the detected double-circle pattern, a region inside an inner circle of the double-circle pattern is specified as the crystalline lens portion, and a region between the inner circle and an outer circle of the double-circle pattern is specified as the iris portion for each of the taken images. As illustrated in FIG. 5, the iris is present around the crystalline lens. The iris portion denotes a portion of the fish eye corresponding to the iris, and the crystalline lens portion denotes a portion of the fish eye corresponding to the crystalline lens.

When a circular arc is specified from a boundary line defined by the edge portion which has been obtained by applying the first derivation filter, the pattern matching may be performed by calculating a circle center from the specified circular arc, and by employing concentric circles, of which centers are aligned with the calculated center, as candidates to be fitted to the double-circle pattern. A manner of calculating the circle center from the edge portion is described here with reference to FIG. 6. One or more intermittent curves resulting from connecting the edge portions (i.e., portions where the spatial gradient of the luminance is large), which are obtained by applying the first derivation filter, are calculated for an obtained image (e.g., an ultraviolet image after the lapse from 20 minutes from death of a fish in an example of FIG. 6). A tangential line (dotted line in FIG. 6) with respect to a point on each curve is calculated, and a normal line (solid line in FIG. 6) passing that point and being perpendicular to the relevant tangent line is calculated. The calculation of such a normal line is executed for each point, and a point where the plural normal lines intersect is calculated as the center of the circle (i.e., center coordinates of the fish eye). Unlike a human eye ball, the fish eye has neither eyelashes nor eyelid. Therefore, the center of the fish eye on the image can be specified by the above-described method. When discriminating the iris portion and the crystalline lens portion in the fish eye by employing the double-circle pattern, for example, the discrimination may be performed by setting a boundary based on a luminance distribution such that, between the iris portion and the crystalline lens portion, there is a luminance difference (difference in average luminance value between those portions) of a specific amount or more.

After the image data of the iris portions and the crystalline lens portions of the left and right fish eyes have been extracted by the analysis unit 3, the calculation unit 4 calculates the freshness index value A for evaluation of freshness of the fish for each of the left and right sides based on the average luminance value of the extracted iris portion and the average luminance value of the extracted crystalline lens portion (processing step S3). Here, the average luminance value of the iris portion is an average value of luminance values of individual pixels that constitute the iris portion in the image, and the average luminance value of the crystalline lens portion is an average value of luminance values of individual pixels that constitute the crystalline lens portion in the image. However, a region providing the basis for calculation of the average luminance value of the iris portion is not limited the entire iris portion in some cases. For example, the above-mentioned region may be a region remained after excepting for a predetermined zone from the boundary between the iris portion and the crystalline lens portion. Similarly, a region providing the basis for calculation of the average luminance value of the crystalline lens portion is not limited to the entire crystalline lens portion in some cases. For example, the above-mentioned region may be a region remained after excepting for a predetermined zone near the boundary between the iris portion and the crystalline lens portion.

Alternatively, the region providing the basis for calculation of the average luminance value of the iris portion may be a region remained after excepting for a region in which the luminance value is not less than a specific upper limit threshold or not more than a specific lower limit threshold. Similarly, the region providing the basis for calculation of the average luminance value of the crystalline lens portion is not limited to the entire crystalline lens portion in some cases, and it may be a region remained after excepting for a region in which the luminance value is not less than a specific upper limit threshold or not more than a specific lower limit threshold.

The freshness index value A is a value obtained by normalizing the average luminance value of the iris portion by employing the average luminance value of the crystalline lens portion. The freshness index value A is, for example, a value obtained by subtracting the average luminance value of the crystalline lens portion from the average luminance value of the iris portion (i.e., a difference in the average luminance value between the iris portion and the crystalline lens portion). As another example, the freshness index value A may be a value obtained by dividing the difference in the average luminance value between the iris portion and the crystalline lens portion by the average luminance value of the crystalline lens portion, or a ratio of the average luminance value of the iris portion to the average luminance value of the crystalline lens portion. Luminance of each of the iris portion and the crystalline lens portion, the luminance providing the basis of the freshness index value A, will be described below with reference to FIGS. 7 to 9 that represent results of experiments using fish.

Figure 7:
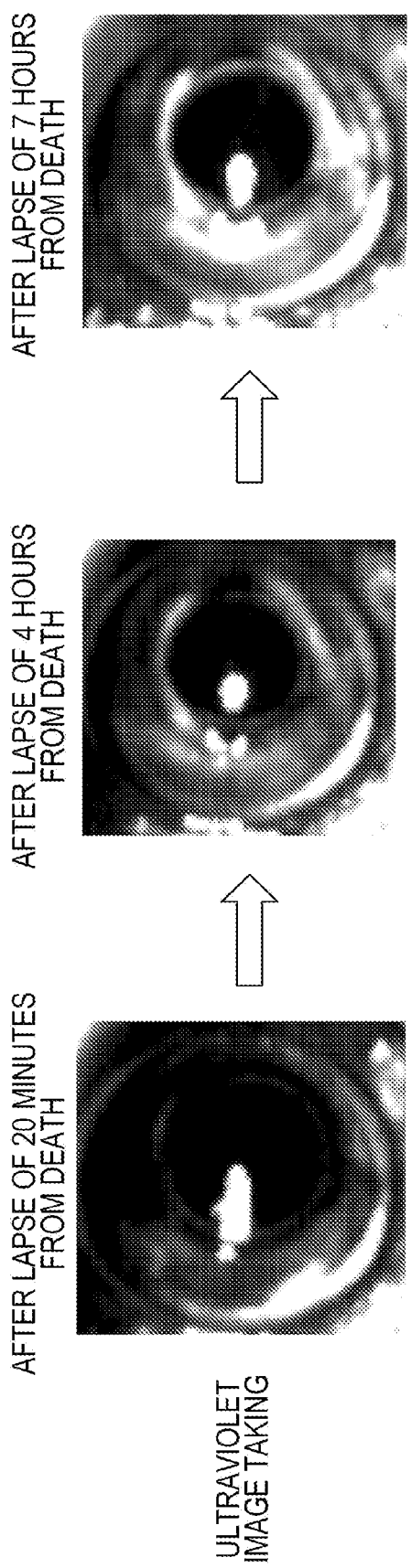
FIG. 7 represents images of an eye of a fish that has been preserved at an ordinary temperature, the images being taken by an ultraviolet camera.

FIG. 7 represents images of an eye of a fish that has been preserved under preservation environment at an ordinary temperature (air temperature of 20° C.) and a humidity of 100%, the images being taken by an ultraviolet camera. FIG. 7 sequentially represents an image taken after the lapse of 20 minutes from death of the fish, an image taken after the lapse of 4 hours from the death of the fish, and an image taken after the lapse of 7 hours from the death of the fish. As seen from FIG. 7, just the iris portion of the fish eye undergoes a color change and becomes whitey at a time after the lapse of 4 hours from the death.

Figure 8:
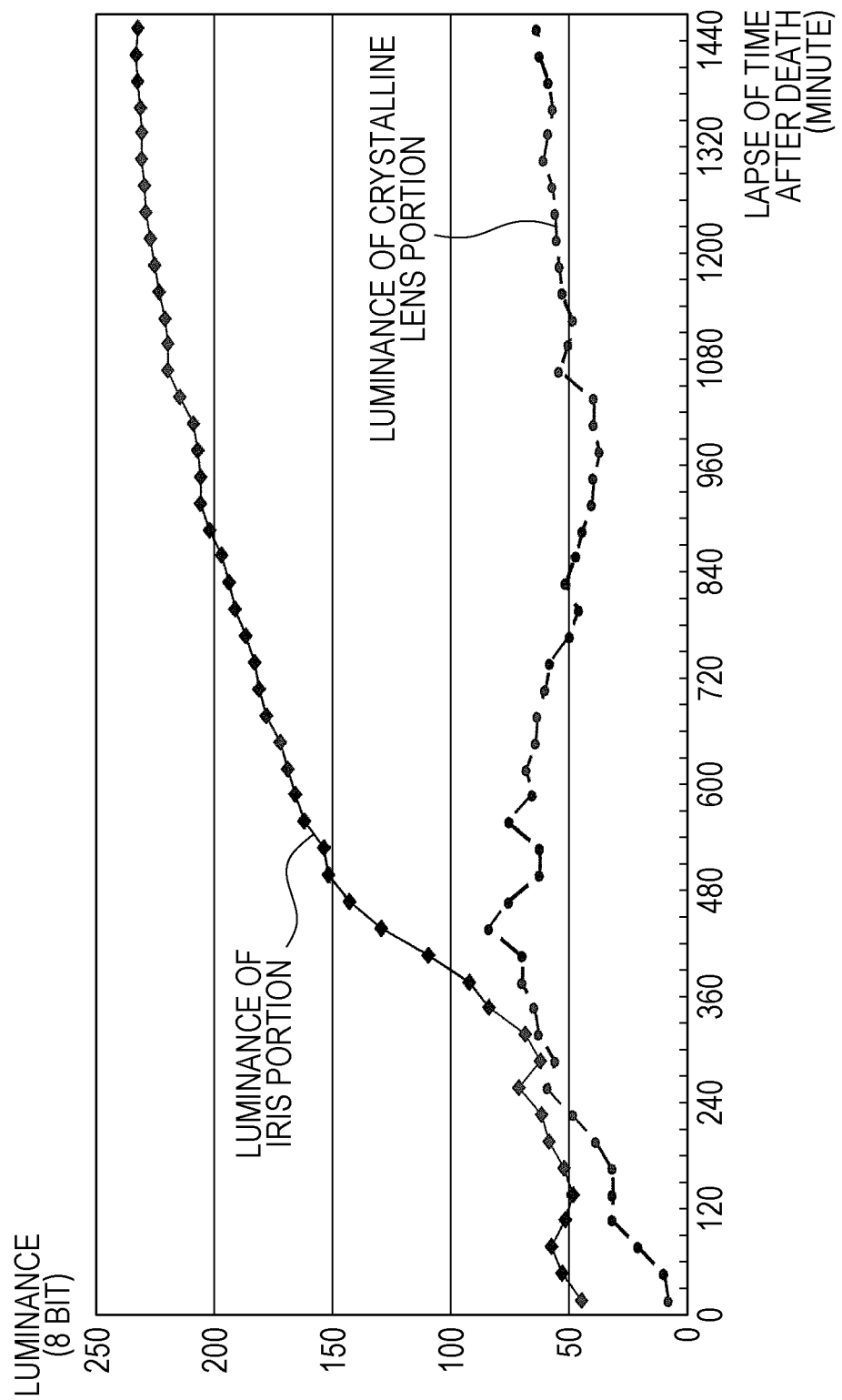
FIG. 8 is a graph plotting time-lapsed changes in luminance of an iris portion and luminance of a crystalline lens portion of the fish eye.

FIG. 8 is a graph plotting time-lapsed changes in luminance of an iris portion and luminance of a crystalline lens portion of an eye of a fish that has been preserved under preservation environment at an ordinary temperature (air temperature of 20° C.) and a humidity of 100%. There is a tendency that, after 6 hours from the death, change in the luminance of the crystalline lens portion with the lapse of time is small, whereas the luminance of the iris portion increases with the lapse of time. It is also confirmed from experiments that a rate of the change in luminance with the lapse of time is different depending on the kind of fish. It is further confirmed from experiments that, for the same kind of fish, a degree of the color change of the iris portion to white with the lapse of time is similar in any individuals although an absolute value of the luminance may be different depending on the differences among the individual fishes.

Figure 9:
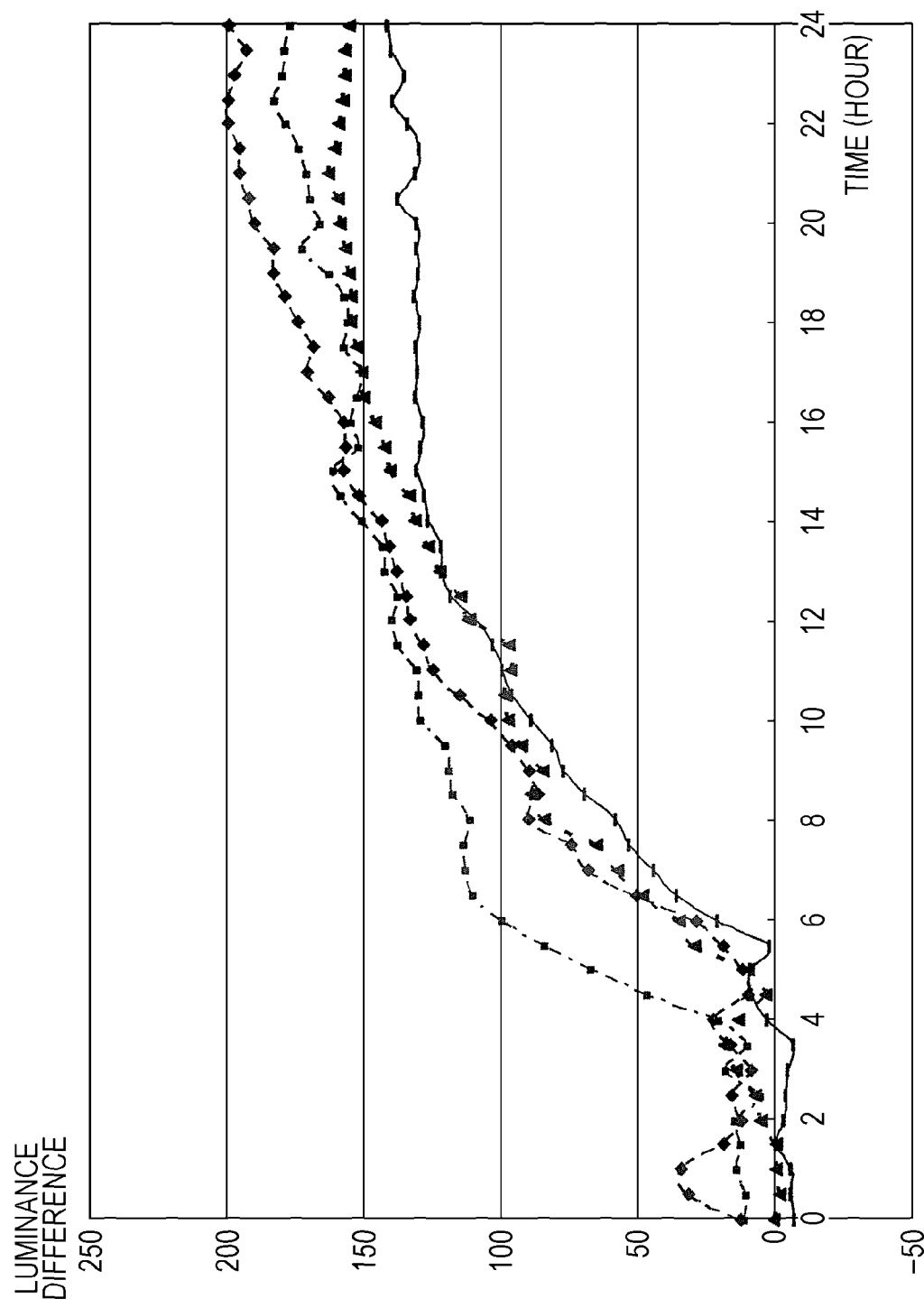
FIG. 9 is a graph plotting time-lapsed changes in differences between average luminance values of iris portions and average luminance values of crystalline lens portions of plural fishes.

FIG. 9 is a graph plotting time-lapsed changes in differences between average luminance values of iris portions and average luminance values of crystalline lens portions of plural (four) fishes that have been preserved under preservation environment at an ordinary temperature (air temperature of 20° C.) and a humidity of 100%. Regardless of variations among individual fishes, the difference in the average luminance value tends to increase at comparable rates with the lapse of time for all the fishes. The difference in the average luminance value, plotted in FIG. 9, is obtained by normalizing the average luminance value of the iris portion by employing the average luminance value of the crystalline lens portion. Such normalization can eliminate influences of differences among individual fishes to some extent, which appear on the image. It is to be noted that the influences of differences among the individual fishes involve not only influences attributable to differences in brightness of the fish eyes themselves, but also influences attributable to differences in image-taking conditions, such as image-taking distances, which may occur depending on differences among, e.g., shapes and sizes of the individual fishes. Thus, the freshness index value A obtained by normalizing the average luminance value of the iris portion by employing the average luminance value of the crystalline lens portion is correlated to the lapse of time from the death of the fish, and it can be used as an index indicating freshness of the fish.

The luminance of the iris portion in the ultraviolet image of the fish eye and the preservation environment will be described below with reference to FIGS. 10 and 11.

Figure 10:
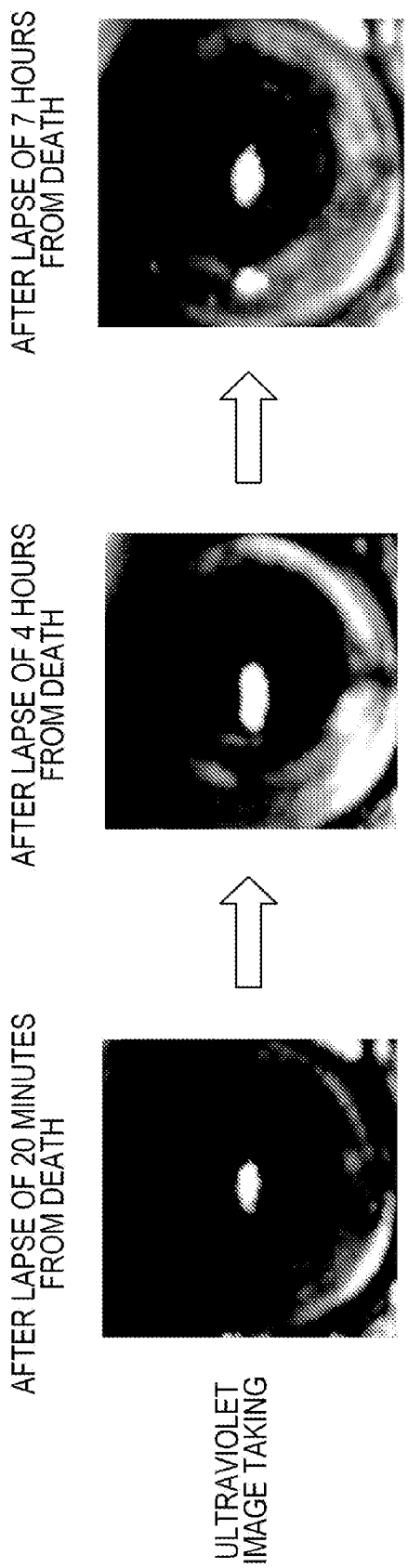
FIG. 10 represents images of an eye of a fish that has been refrigerated, the images being taken by an ultraviolet camera.
Figure 11:
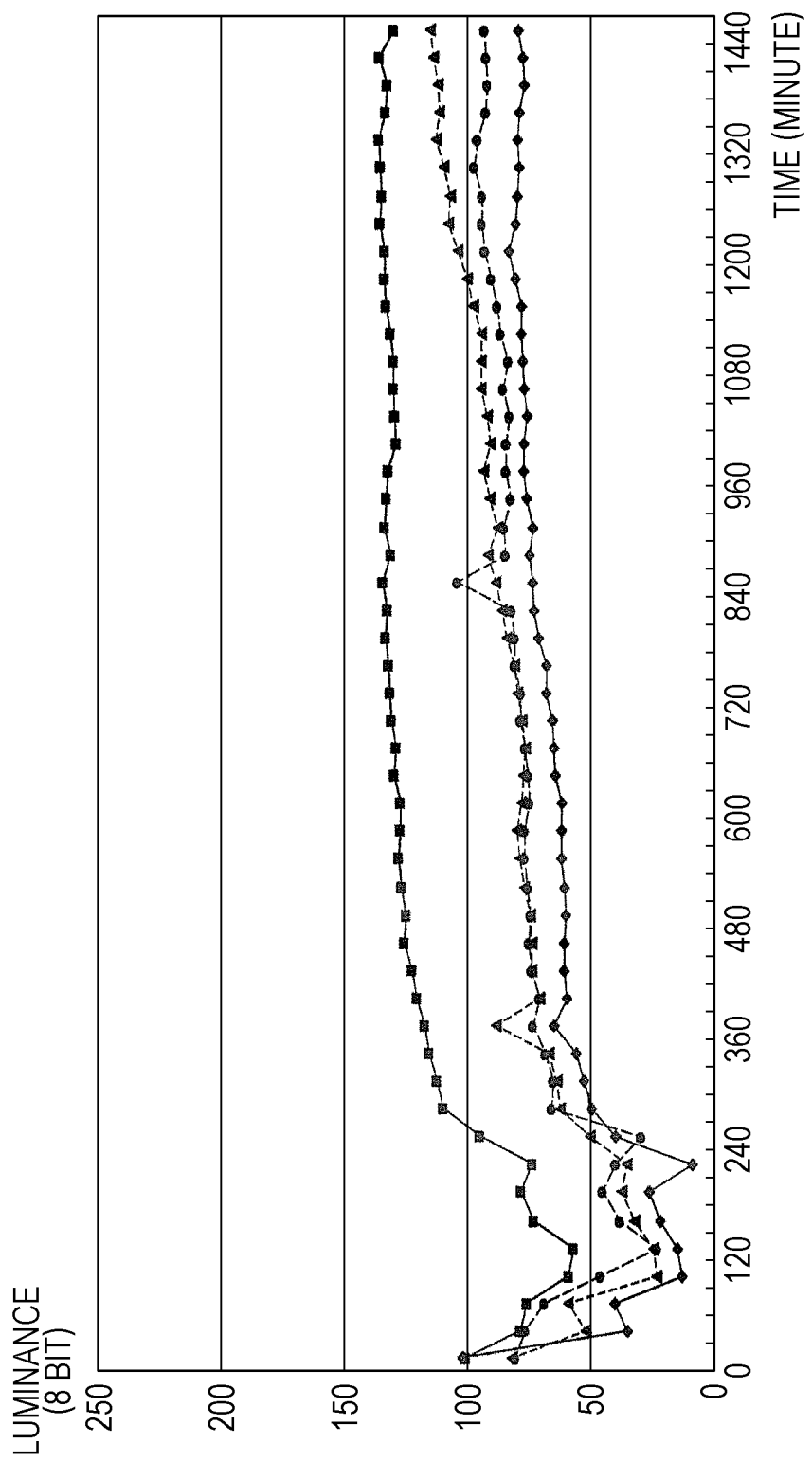
FIG. 11 is a graph plotting time-lapsed changes in average luminance values of iris portions of plural fishes that have been refrigerated.

FIG. 10 represents images of an eye of a fish that has been refrigerated under preservation environment at an air temperature of 4° C. and a humidity of 100%, the images being taken by an ultraviolet camera. FIG. 11 is a graph plotting time-lapsed changes in luminance of iris portions of plural (four) fishes that have been refrigerated under preservation environment at air temperature of 4° C. and a humidity of 100%. As is apparent from FIGS. 10 and 11, in the case of the preservation under refrigeration, a speed of whitening of the iris portion with the lapse of time is slower, namely a speed of increase in the luminance of iris portion is slower, than in the case of the preservation at the ordinary temperature, illustrated in FIGS. 6 and 7. In other words, the speed of whitening of the iris portion is different depending on different preservation environments (e.g., different preservation temperatures). Furthermore, it is confirmed from experiments that, depending on different preservation environments, a tendency of time-lapsed change in the freshness index value A, which reflects the luminance of the iris portion, is also different. By utilizing such a tendency, the preservation environment information output device 100 determines the preservation environment of the fish with attention focused on the difference in preservation environment between the left and right sides, which appears in a bilateral difference in freshness of the fish between the left and right sides. Such determination is made, for example, by comparing the freshness index value A obtained from the left eye image, which indicates the freshness at the left side, with the freshness index value A obtained from the right eye image, which indicates the freshness at the right side, and determining whether the preservation environments of the fish are under the same conditions (e.g., at the same preservation temperature) between the left and right sides of the fish body.

After the freshness index value A has been calculated by the calculation unit 4 in the processing step S3 for each of the left and right sides of the fish, the determination unit 2 determines, in accordance with the information 8 for determination, the preservation environment of the fish as follows depending on the freshness index values A at the left and right sides (processing steps S4 to S6). FIG. 12 is a table representing a bilateral difference in the freshness index value A and information indicating the preservation environment of the fish, as an example of the information 8 for determination, in a linked manner. Furthermore, when the freshness index value A is given as a value obtained by dividing the difference between the average luminance value of the iris portion and the average luminance value of the crystalline lens portion by the average luminance value of the crystalline lens portion, or as a ratio of the average luminance value of the iris portion to the average luminance value of the crystalline lens portion, the determination can be made in a similar way by preparing a table corresponding to the selected case. In accordance with the information 8 for determination, the determination unit 2 determines the bilateral difference in the freshness index value A is smaller than a specific threshold A1 (processing step S4), and if the bilateral difference in the freshness index value A is smaller than the specific threshold A1, it determines that the fish has been preserved under substantially the same conditions at the left and right sides (processing step S5). If the bilateral difference in the freshness index value A is not smaller than the specific threshold A1, the determination unit 2 determines that the fish has not been preserved under substantially the same conditions at the left and right sides (processing step S6). More specifically, in the processing step S6, the freshness index values A at the left and right sides are compared with each other. If the freshness index value A at the left side is higher, it is determined that the fish has been preserved under bad conditions (e.g., in a not refrigerated state) at the left side. If the freshness index value A at the right side is higher, it is determined that the fish has been preserved under bad conditions at the right side. Factors causing the state that the fish has been preserved under bad conditions just at one side are, for example, imbalance of temperature inside a refrigerator or contact of just one side of the fish body with a cold reserving material. When the preservation environment information output device 100 determines that the fish has been preserved under bad conditions at one side, there may be a room for improvement in the preservation environment of the fish. The information indicating the determination result by the determination unit 2 (i.e., the information indicating the preservation environment of the fish) is output by displaying the relevant information on the display 15 (processing step S7). As a result, a user of the preservation environment information output device 100 can recognize whether the preservation environment of the fish has been proper. When it is determined that the fish has been preserved under substantially the same conditions at the left and right sides, the preservation environment may be determined as follows; namely the fish has been preserved at substantially the same temperature at the left and right sides. When it is determined that the fish has not been preserved under substantially the same conditions at the left and right sides, the preservation environment may be determined as follows; namely the fish has not been preserved at substantially the same temperature at the left and right sides.

Figure 13:
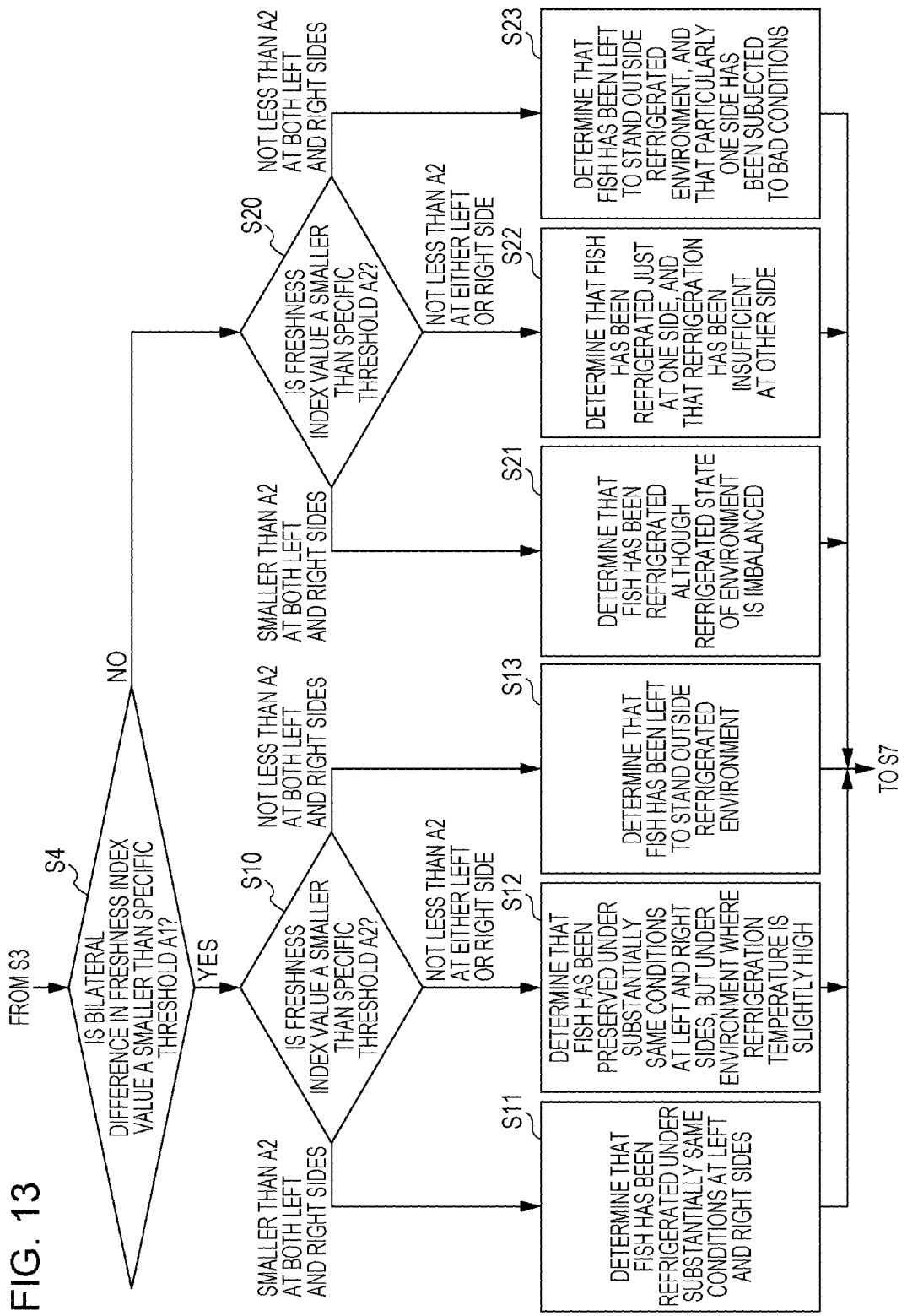
FIG. 13 is a flowchart representing an example of a preservation environment determination process.

The determination regarding the preservation environment of the fish by the determination unit 2 in the above-described processing steps S4 to S6 (see FIG. 4) may be modified as illustrated in FIG. 13. In other words, the preservation environment can be determined in more detail by, subsequent to the processing step S4 determining whether the bilateral difference in the freshness index value A is smaller than the specific threshold A1, by determining whether the freshness index value A is smaller than a specific threshold A2 (processing steps S10 and S20).

More specifically, in the case of the bilateral difference in the freshness index value A being smaller than the specific threshold A1, if it is determined in a processing step S10 that the freshness index values A at the left and right sides are both smaller than the specific threshold A2, the determination unit 2 determines that the fish has been refrigerated under substantially the same conditions in a balanced state at the left and right sides (processing step S11). If the freshness index value A just at one of the left and right sides is not less than the specific threshold A2, the determination unit 2 determines that the fish has been preserved under substantially the same conditions at the left and right sides, but the refrigeration temperature is slightly high, and that the refrigeration is insufficient (processing step S12). If the freshness index values A at the left and right sides are both not less than the specific threshold A2, the determination unit 2 determines that the fish has been left to stand outside the refrigerated environment (processing step S13). In the case of the bilateral difference in the freshness index value A being not smaller than the specific threshold A1, if it is determined in a processing step S20 that the freshness index values A at the left and right sides are both smaller than the specific threshold A2, the determination unit 2 determines that the fish has been refrigerated, although the conditions of the fish at the left and right sides are not substantially the same and the refrigerated state of the preservation environment is imbalanced (processing step S21). If the freshness index value A just at one of the left and right sides is not less than the specific threshold A2, the determination unit 2 determines that the fish has been refrigerated just at the relevant one side, and that the refrigeration is insufficient at the other side (processing step S22). If the freshness index values A at the left and right sides are both not less than the specific threshold A2, the determination unit 2 determines that the fish has been left to stand outside the refrigerated environment, and that particularly one side of the fish has been subjected to bad conditions (processing step S23). The results determined in the processing steps S11 to S13 and the processing steps S21 to S23 are output in the processing step S7 (see FIG. 4).

Here, the specific threshold A1 and the specific threshold A2 are previously determined, for example, through learning based on experimental results. For many fishes having been preserved under various preservation environments, respective average luminance values of the iris portions and the crystalline lens portions of fish eyes at both the left and right sides per kind of fish are measured at successive points in time lapsed after the death, and an average value of the freshness index values A and a standard deviation value indicating a variance of the freshness index values A at the successive points in time are calculated and recorded for the many fishes. For example, a normal distribution is assumed from the average value and the standard deviation value of the freshness index values A, which have been recorded per kind of fish at the successive points in the lapsed time, and the specific threshold A1 is determined which is used to discriminate the case where the preservation conditions are different between the left and right sides, e.g., the case where one of the left and right sides has been refrigerated and the other side has been preserved at an ordinary temperature, and the case where the preservation conditions are the same between the left and right sides. Different preservation conditions between the left and right sides imply that the preservation environment is imbalanced. Moreover, based on results similarly measured for many fishes, the specific threshold A2 is determined, per kind of fish at the successive points in the lapsed time, as a value that is estimated to be taken at maximum by the freshness index value A when the fish has been refrigerated properly. The specific threshold A1 and the specific threshold A2 thus determined per kind of fish at the successive points in time lapsed from the death are stored, for example, in the memory of the preservation environment information output device 100. When the preservation environment is to be determined by the determination unit 2 of the preservation environment information output device 100, corresponding one of the specific threshold A1 and the specific threshold A2 is selected depending the kind of fish and the time lapsed from the death, which are input through the input device, and is used in making the determination. Under certain conditions (e.g., operating conditions where the kind of fish and the time lapsed from the death can be specified), the specific threshold A1 or the specific threshold A2 may be fixedly determined without input operations. Furthermore, the specific threshold A1 may be set to, e.g., a value allowing the preservation conditions at the left and right sides to be regarded as being the same when the temperature difference between the left and right sides is within ±5° C., for example.

In the above description, the determination unit 2 of the preservation environment information output device 100 determines the preservation state of the fish based on the freshness index values A (each obtained by normalizing the average luminance value of the iris portion by employing the average luminance value of the crystalline lens portion) at the left and right sides of the fish. Alternatively, on the premise that conditions of the ultraviolet sources and the ultraviolet cameras at the left and right sides are set to the same ones, the determination unit 2 may determine the preservation state of the fish based on the bilateral difference in the average luminance value of the iris portion of the fish without employing the average luminance value of the crystalline lens portion. For example, when the bilateral difference in the average luminance value of the iris portion of the fish is not more than a certain value, the determination unit 2 may determine that the fish has been preserved under the same conditions at the left and right sides. When the bilateral difference is larger than the certain value and the average luminance value of the iris portion is higher at the left side, the determination unit 2 may determine that the fish has been possibly refrigerated just at the right side. On the other hand, when the average luminance value of the iris portion is higher at the right side, the determination unit 2 may determine that the fish has been possibly refrigerated just at the left side.

While, in the above-described example, the images of the left and right fish eyes are taken by the ultraviolet cameras 11a and 11b at the same time, the images may be taken not at the same timing in some cases. Furthermore, instead of taking an image by each ultraviolet camera once, a plurality of images may be taken while the sample setting unit 19 on which the fish is set is moved at intervals of a short time (e.g., 5 sec) a little by a little (e.g., in units of 5 mm) between both the ultraviolet cameras. For respective sets of plural left eye images and plural right eye images thus obtained, the freshness index value A may be calculated from results averaging luminance values of the iris portions and luminance values of the crystalline lens portions in those images, and the preservation environment may be determined depending on a bilateral difference in the freshness index value A. There is a possibility that the luminance value, the freshness index value A, etc. can be obtained with higher reliability by taking a plurality of images and calculating an average value from the plural images as described above.

Thus, the preservation environment information output device 100 can determine the preservation environment of a fish after death by taking images of left and right eyes of the fish with two ultraviolet sources and two ultraviolet cameras, analyzing the taken images in the computer 14, and making the determination based on a bilateral difference in, e.g., an average luminance value of the iris portion between the left and right eyes of the fish.

Second Embodiment

A preservation environment information output device 200 as another embodiment of the present disclosure will be described below with reference to the drawings. The preservation environment information output device 200 is constituted by modifying the specific configuration of the image taking unit 1 in the preservation environment information output device 100 according to the first embodiment. Description of the same components as those in the preservation environment information output device 100 is omitted here.

Figure 14:
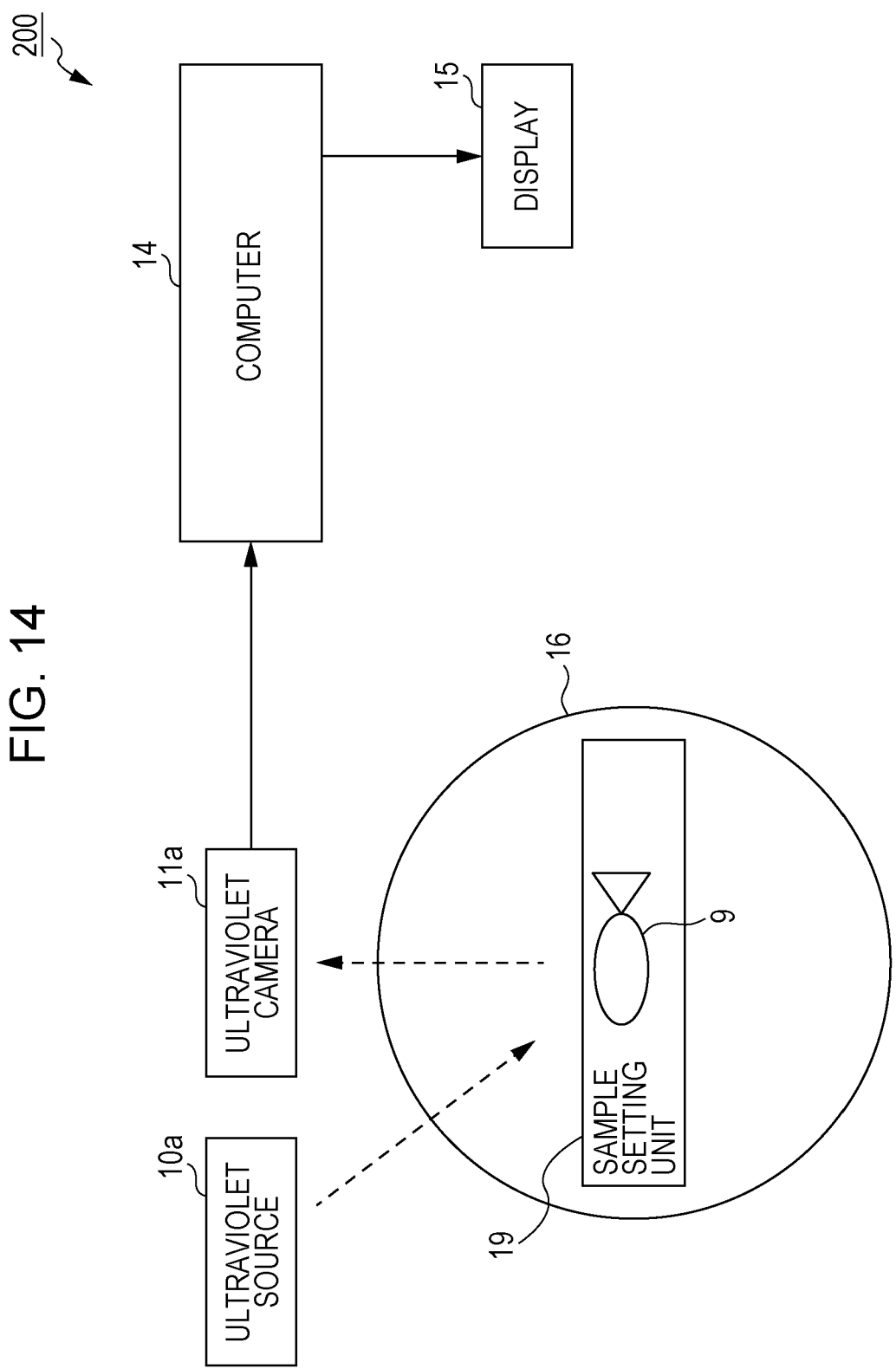
FIG. 14 is a hardware configuration diagram of a preservation environment information output device according to a second embodiment.
Figure 15:
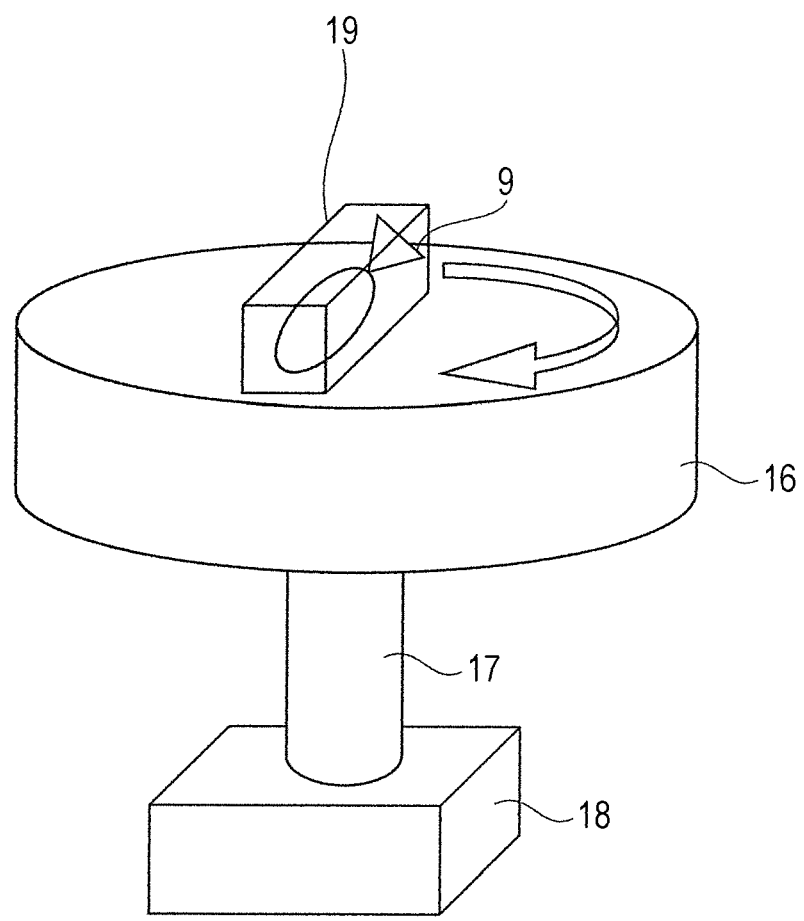
FIG. 15 is a schematic view of a turntable on which a sample setting unit according to the second embodiment is mounted.

FIG. 14 is a hardware configuration diagram of the preservation environment information output device 200 according to the second embodiment. FIG. 15 is a schematic view of a turntable on which a sample setting unit 19 in the preservation environment information output device 200 is mounted.

As illustrated in FIGS. 14 and 15, the preservation environment information output device 200 includes a turntable 16, a rotating shaft 17, and a rotary motor 18 in addition to an ultraviolet source 10a, an ultraviolet camera 11a, a computer 14, a display 15, and the sample setting unit 19, which are the same as those in the preservation environment information output device 100 according to the first embodiment. Stated another way, while the preservation environment information output device 100 has two image-taking systems constituted by two ultraviolet sources and two ultraviolet cameras, the preservation environment information output device 200 has one image-taking system and includes the sample setting unit 19 that is mounted on the turntable 16 rotated by the rotary motor 18. The rotary motor 18 is designed to rotate the turntable 16 through 180 degrees, for example, each time a switch is turned on. The switch may be controlled from the computer 14. A left-side image (left eye image) and a right-side image (right eye image) of a fish body set on the sample setting unit 19 are generated by performing twice the emission of ultraviolet rays from the ultraviolet source 10a and the image-taking with the ultraviolet camera 11a in the one image-taking system while the turntable 16 is rotated through 180 degrees. For example, after taking the left eye image, the turntable 16 is rotated through 180 degrees in a short time (e.g., within 10 sec), and the right eye image is taken. Processing (processing steps S2 to S7) to, after the determination unit 2 obtains the left eye image and the right eye image generated as described above, extract image data of, e.g., the iris portion of the fish eye, to calculate the freshness index value A, and to determine the preservation environment of the fish is the same as that explained in the first embodiment. As a result, even with the preservation environment information output device 200 having just one image-taking system, information indicating the preservation environment of the fish is displayed on the display 15. By employing just one image-taking system as in this embodiment, the image taking conditions, such as the distances from the light source and the camera to the fish, can be physically unified when the left eye image and the right eye image are taken. It is to be noted that, by repeating the rotation of the turntable 16, respective sets of plural left eye images and plural right eye images may be taken and averaged to make the determination. In other words, the preservation environment of the fish may be determined by comparing data for the left and right sides by employing an average value of luminance values (or freshness index values A) of the fish eye based on all of the taken left eye images and an average value of luminance values (or freshness index values A) of the fish eye based on all of the taken right eye images. There is a possibility that the determination result can be obtained with higher reliability by taking a plurality of images as described above.

When two systems of light sources and cameras are mounted at both the left and right sides of the fish as in the first embodiment and the sample setting unit 19 is placed on the turntable 16 as in the second embodiment, a plurality of images of the fish at the same side are taken by the different cameras for each of the left and right sides by rotating the turntable 16 in units of 180 degrees. By employing an average luminance value of all the images taken for each side, even when there is a deviation in the image taking conditions between the left and right sides, the bilateral difference in the luminance value can be calculated free from distortions of the luminance value, which may occur due to the deviation in the image taking conditions. Thus, the preservation environment of the fish can be determined with higher reliability.

Third Embodiment

A preservation environment information output device 300 as still another embodiment of the present disclosure will be described below with reference to the drawings. The preservation environment information output device 300 is constituted by modifying a part of the preservation environment information output device 200 according to the second embodiment. Description of the same components as those in the preservation environment information output device 200 is omitted here.

Figure 16:
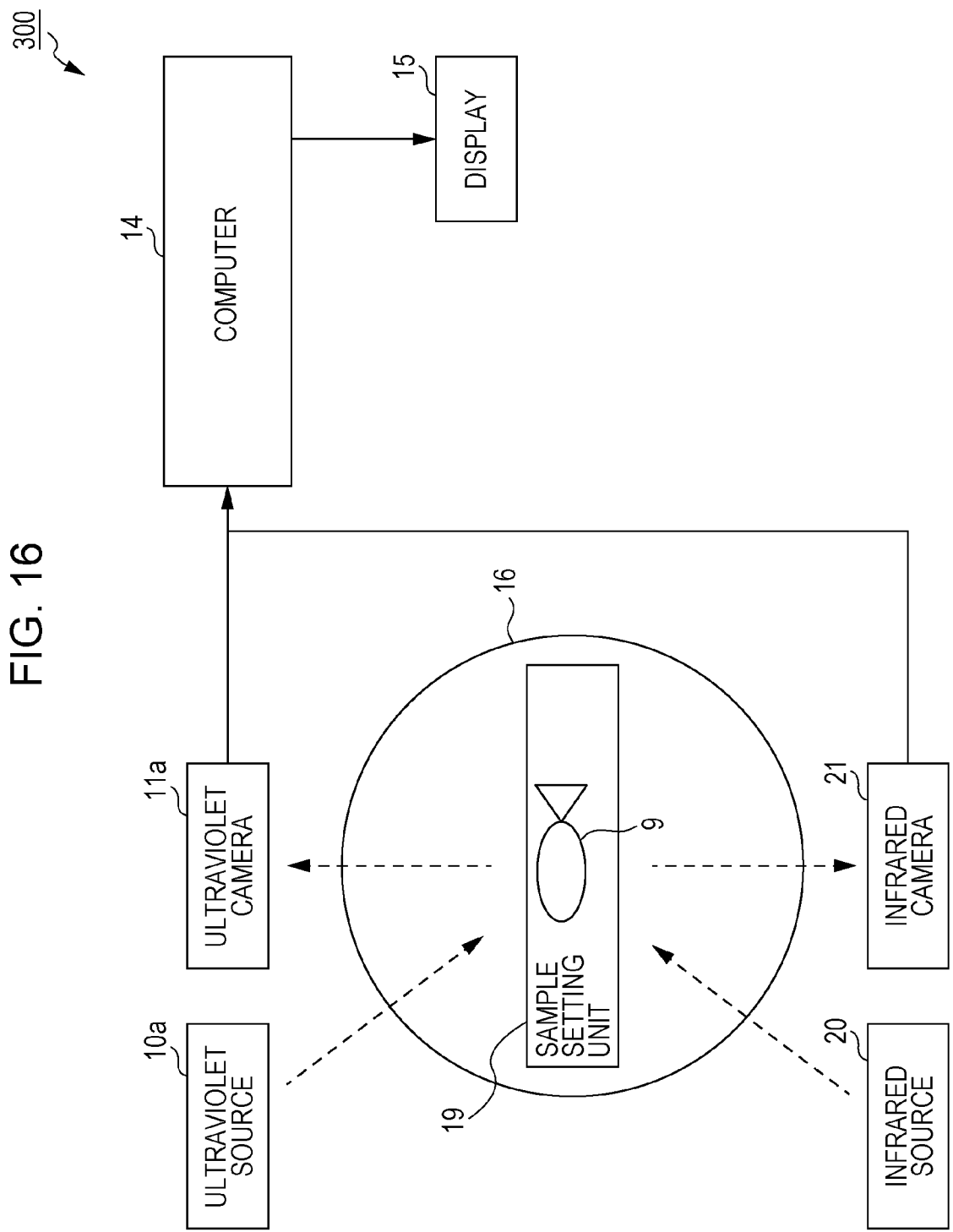
FIG. 16 is a hardware configuration diagram of a preservation environment information output device according to a third embodiment.

FIG. 16 is a hardware configuration diagram of the preservation environment information output device 300 according to the third embodiment.

As illustrated in FIG. 16, the preservation environment information output device 300 includes an infrared source 20 and an infrared camera 21 in addition to an ultraviolet source 10a, an ultraviolet camera 11a, a computer 14, a display 15, a turntable 16, a rotating shaft 17 (see FIG. 15), and a rotary motor 18 (see FIG. 15), which are the same as those in the preservation environment information output device 200 according to the second embodiment. The infrared source 20 and the infrared camera 21 are adapted for an infrared range (e.g., a wavelength band of 700 nm to 1000 nm). The infrared camera 21 receives infrared rays (infrared light), which have been emitted from the infrared source 20 and reflected by a fish, and generates an infrared image.

In the image taking unit 1 of the preservation environment information output device 300, the ultraviolet source 10a emits ultraviolet rays, and the ultraviolet camera 11a takes a left eye image as an ultraviolet image. Furthermore, the infrared source 20 emits infrared rays, and the infrared camera 21 takes a right eye image as an infrared image. Thereafter, the turntable 16 is rotated through 180 degrees within 10 sec, for example, and the image taking unit 1 performs operations of emitting the ultraviolet rays from the ultraviolet source 10a, taking a right eye image, as an ultraviolet image, by the ultraviolet camera 11a, emitting the infrared rays from the infrared source 20, taking a left eye image, as an infrared image, by the infrared camera 21. The determination unit 2 obtains the left eye images and the right eye images that have been generated using the ultraviolet rays and the infrared rays as mentioned above. The analysis unit 3 extracts luminance values of the iris portions from those images, and the calculation unit 4 calculates a freshness index value B instead of the freshness index value A explained in the first embodiment. Then, the determination unit 2 compares the freshness index value B calculated from the left eye image with the freshness index value B calculated from the right eye image (namely, calculates a discrepancy in the freshness index value B between the left and right sides, e.g., a bilateral difference in the freshness index value B or ratio thereof between the left and right sides), determines the preservation environment of the fish, and displays a determination result on the display 15. Because the operation of obtaining and utilizing the freshness index value B instead of the freshness index value A is performed, a control program stored in a memory of the computer 14 and executed by a processor is partly modified from the control program used in the first embodiment.

Here, the freshness index value B calculated by the calculation unit 4 for each of the left eye image and the right eye image is a value obtained by normalizing an average luminance value of the iris portion in the ultraviolet image by employing an average luminance value of the iris portion in the infrared image. The freshness index value B is, e.g., a value obtained by subtracting the average luminance value of the iris portion in the infrared image from the average luminance value of the iris portion in the ultraviolet image (i.e., a difference between the average luminance values of the iris portions in both the images). Alternatively, the freshness index value B may be a value obtained by dividing the difference between the average luminance values of the iris portions in both the images by the average luminance value of the iris portion in the infrared image, or a ratio of the average luminance value of the iris portion in the ultraviolet image to the average luminance value of the iris portion in the infrared image. The freshness index value B may be calculated by employing a luminance value of a fish eye including the iris portion instead of the luminance value of the iris portion.

Luminance of the iris portion in each of the ultraviolet image and the infrared image, the luminance providing the basis of the freshness index value B, will be described below with reference to FIGS. 17 to 19 that represent results of experiments using fish.

Figure 17:
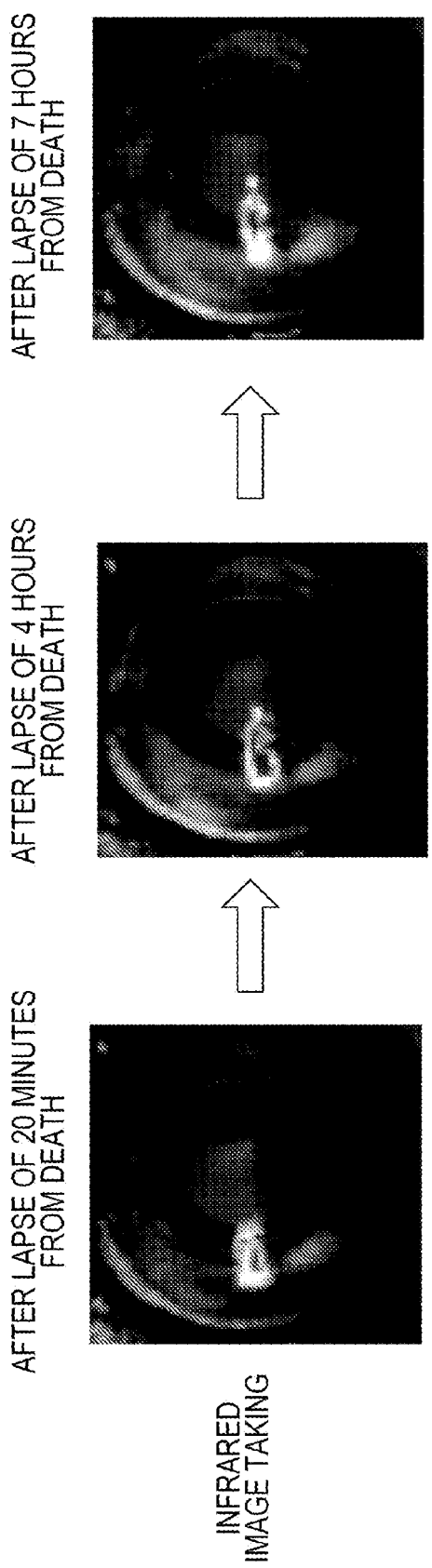
FIG. 17 represents images of a fish eye, the images being taken by an infrared camera.

FIG. 17 represents images of an eye of a fish that has been preserved under preservation environment at an ordinary temperature (air temperature of 20° C.) and a humidity of 100%, the images being taken by the infrared camera. FIG. 17 sequentially represents an image taken after the lapse of 20 minutes from death of the fish, an image taken after the lapse of 4 hours from the death of the fish, and an image taken after the lapse of 7 hours from the death of the fish. Although, in the ultraviolet images illustrated in FIG. 7, the iris portion of the fish eye undergoes a color change and becomes whitey at a time after the lapse of 4 hours from the death, significant luminance change with the lapse of time does not appear in the iris portion and the other portion of the fish eye in the infrared images as illustrated in FIG. 17.

Figure 18:
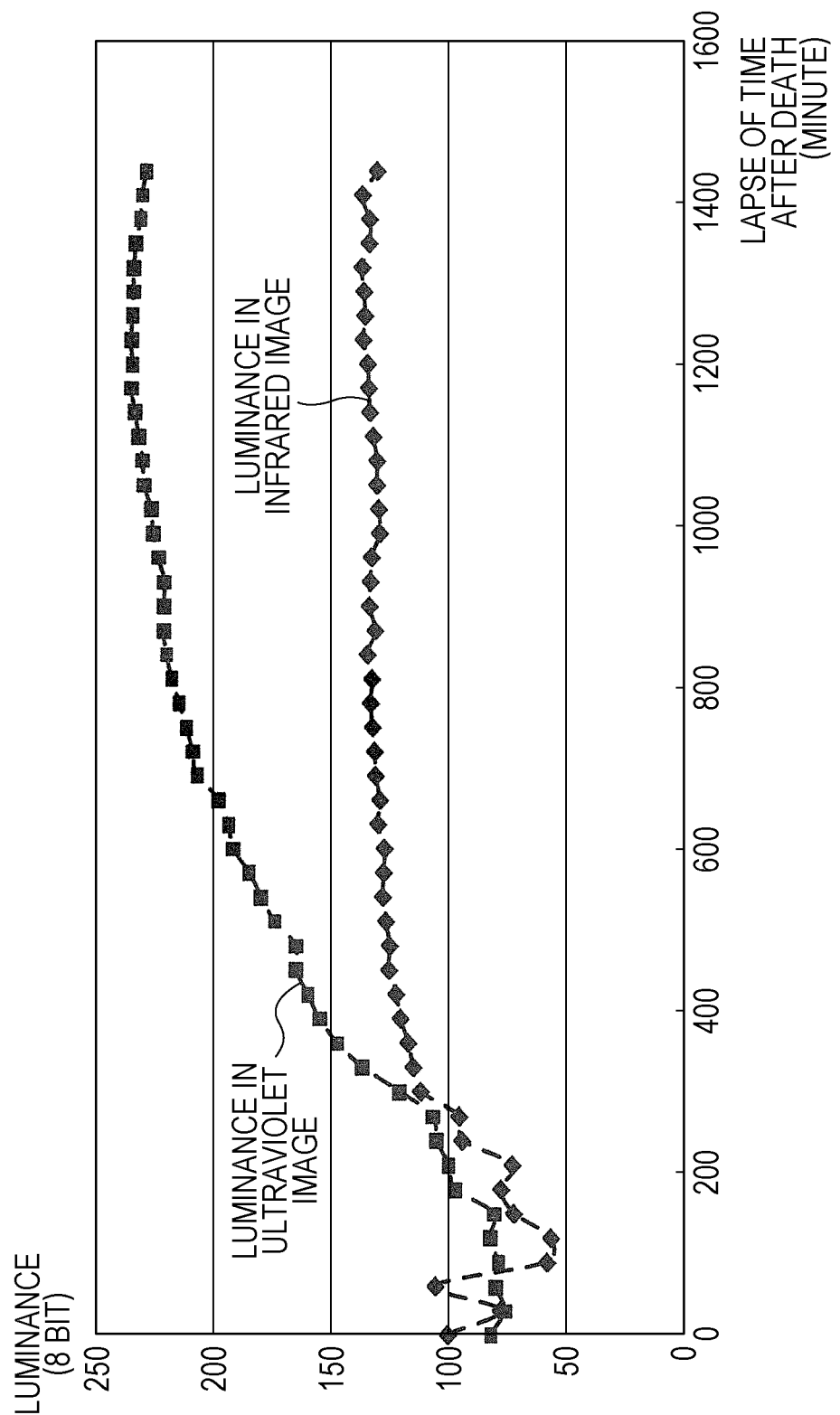
FIG. 18 is a graph plotting time-lapsed changes in luminance of an iris portion in an ultraviolet image and an infrared image.

FIG. 18 is a graph plotting time-lapsed changes in luminance of an iris portion of a fish in the ultraviolet image and the infrared image, the fish having been preserved under preservation environment at an ordinary temperature (air temperature of 20° C.) and a humidity of 100%. As seen from FIG. 18, the luminance of the iris portion in the ultraviolet image is significantly changed with the lapse of time, whereas the luminance of the iris portion in the infrared image is changed less with the lapse of time.

FIG. 19 is a graph plotting time-lapsed changes in differences between average luminance values of iris portions in the ultraviolet images and average luminance values of iris portions in the infrared images for plural (four) fishes that have been preserved under preservation environment at an ordinary temperature (air temperature of 20° C.) and a humidity of 100%. Regardless of variations among individual fishes, the difference in the average luminance value between both the images tends to increase at comparable rates with the lapse of time for all the fishes. The difference in the average luminance value between both the images, plotted in FIG. 19, is obtained by normalizing the average luminance value of the iris portion in the ultraviolet image by employing the average luminance value of the iris portion in the infrared portion. Such normalization can eliminate influences of differences among the individual fishes to some extent, which appear on the image. It is to be noted that the influences of differences among the individual fishes involve not only influences attributable to differences in brightness of the fish eyes themselves, but also influences attributable to differences in image-taking conditions, such as image-taking distances, which may occur depending on differences among, e.g., shapes and sizes of the individual fishes. Thus, the freshness index value B obtained by normalizing the average luminance value of the iris portion in the ultraviolet image by employing the average luminance value of the iris portion in the infrared image is correlated to the lapse of time from the death of the fish, and it can be used as an index indicating freshness of the fish.

To determine the preservation environment of the fish based on the freshness index values B at the left and right sides, the determination unit 2 may utilize, e.g., a table storing the bilateral difference in the freshness index value B and information indicating the preservation environment of the fish in a linked manner similarly to the information 8 for determination, which has been described in the first embodiment. Such a table can be prepared in advance based on experimental results, for example.

Thus, the preservation environment information output device 300 can determine the preservation environment of a fish after death by analyzing an ultraviolet image and an infrared image of left and right eyes of the fish in the computer 14, and making the determination based on a bilateral difference in, e.g., a luminance value of the iris portion or another eye portion between the left and right eyes of the fish.

Other Embodiments

While several embodiments of the preservation environment information output device have been described above, it is a matter of course that the foregoing embodiments are merely illustrative and they can be modified or practiced in various ways.

Figure 20A:
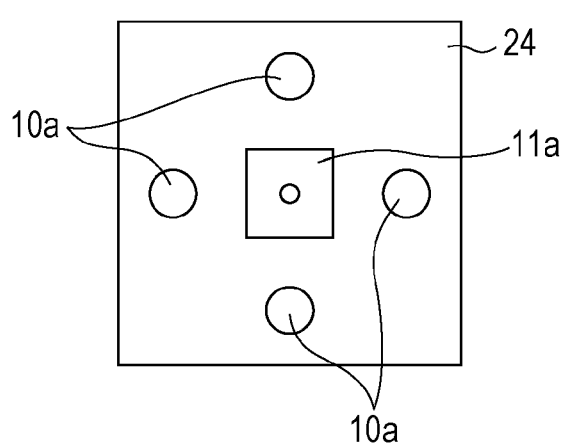
FIGS. 20A and 20B illustrate arrangement of ultraviolet sources and an ultraviolet camera.
Figure 20B:
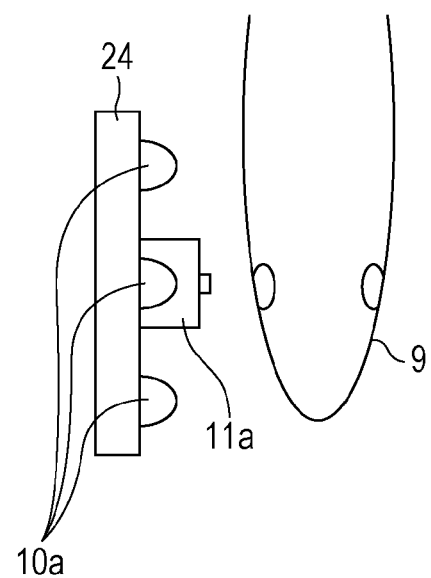
Figure 22:
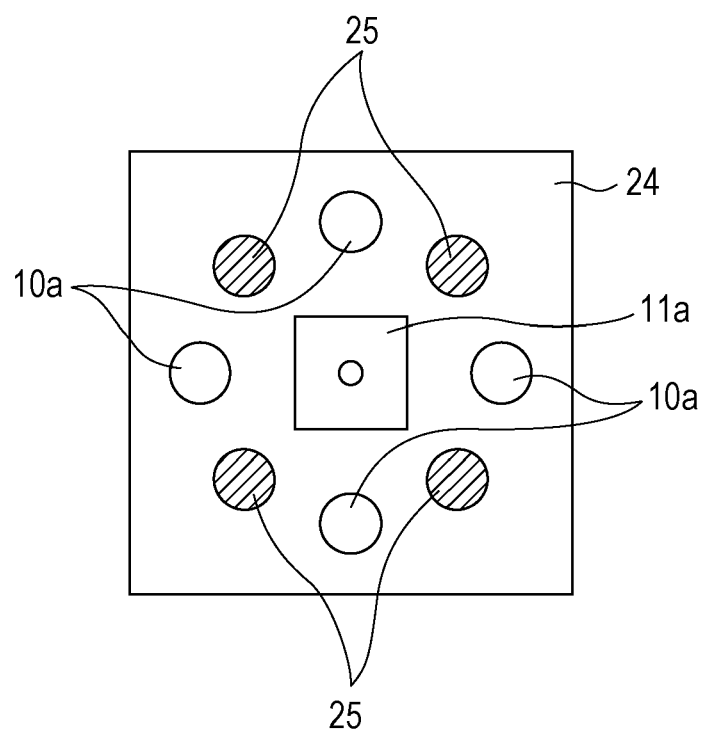
FIG. 22 illustrates arrangement of ultraviolet LEDs and visible light LEDs.

For example, the ultraviolet source 10a and the ultraviolet camera 11a, illustrated in FIG. 3, may be arranged, as illustrated in FIGS. 20A and 20B, in practice. FIG. 20A illustrates the arrangement when viewed from the front of the ultraviolet camera 11a in the image-taking direction, and FIG. 20B illustrates the arrangement when viewed from the side of the ultraviolet camera 11a. As seen, individual ultraviolet LEDs constituting the ultraviolet sources 10a are arranged on an image-taking member mount board 24 in a state surrounding the ultraviolet camera 11a. The ultraviolet camera 11a and the ultraviolet LEDs are connected to the computer 14 such that irradiation and image-taking with ultraviolet rays are performed under control of the computer 14. The above description is similarly applied to the ultraviolet source 10b and the ultraviolet camera 11b, A mechanism for moving a set of the ultraviolet source 10a and the ultraviolet camera 11a (i.e., the image-taking member mount board 24 including them) and a set of the ultraviolet source 10b and the ultraviolet camera 11b (i.e., the image-taking member mount board 24 including them) may be provided in association with the sample setting unit 19 illustrated in FIG. 13, and respective positions of those boards may be adjusted under control of the computer 14 to positions where images of the corresponding fish eyes can be taken by the ultraviolet cameras. For example, as illustrated in FIG. 21, the above-mentioned mechanisms are controlled to adjust image-taking positions such that a fish eye (detected through, e.g., pattern matching with a double-circle pattern), which appears in each of a left eye image and a right eye image taken by the ultraviolet cameras, is located within a predetermined analysis target region in the image. The image-taking position may be adjusted by a user manually moving the fish, instead of being performed under control of the computer 14, such that the ultraviolet camera can take the image of the fish eye at a center. As illustrated in FIG. 22, visible light LEDs 25 for emitting visible lights may be mounted on the image-taking member mount board 24 in addition to the ultraviolet sources 10a, and those visible light LEDs 25 may be used in control to adjust the image-taking position such that the fish eye is located within the predetermined analysis target region. The visible light LEDs 25 are general LEDs. The adjustment of the image-taking position using the visible light LEDs 25 is effective from the viewpoint of eliminating a possibility of an adverse influence (e.g., denaturation of ingredients of the fish eye) on the determination of the preservation environment, which may be caused by irradiation of the fish eye with ultraviolet rays.

Figure 24:
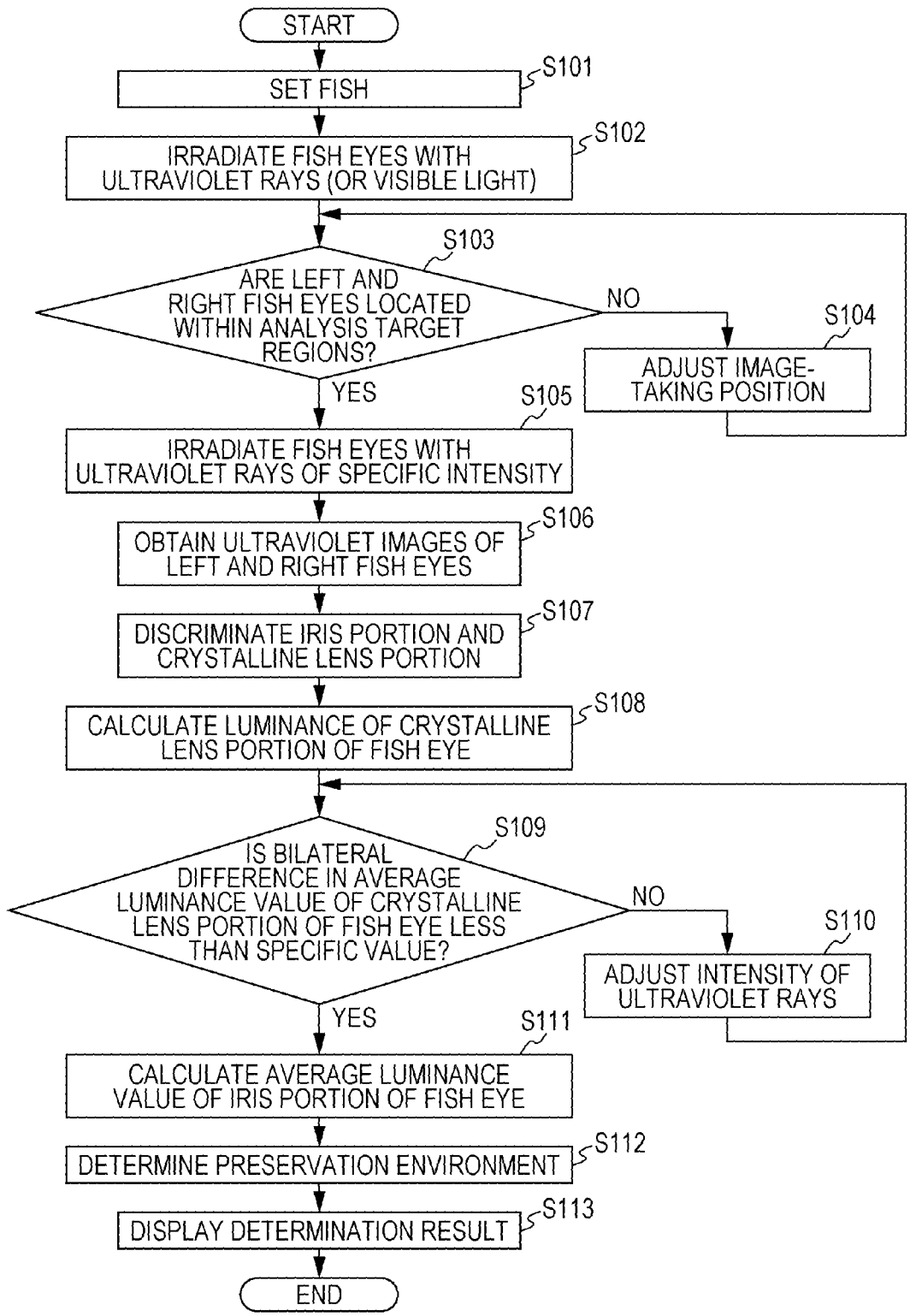
FIG. 24 is a flowchart representing an example of the operation of a preservation environment information output device according to one embodiment.

Furthermore, as illustrated in FIG. 21, a light amount (intensity) of each ultraviolet source may be adjusted such that the average luminance value of the crystalline lens portion of the fish eye in the left eye image and the average luminance value of the crystalline lens portion of the fish eye in the right eye image are substantially the same. Through such an adjustment, effective determination can be made by a method of determining the preservation environment of the fish based on the bilateral difference in the average luminance value of the iris portion of the fish eye (or the bilateral difference in the average luminance value of the fish eye) with omission of the normalization. FIG. 23 illustrates an example of a table representing the information 8 for determination, which is used to make determination in the case of performing the above-described adjustment. FIG. 24 is a flowchart representing an example of the operation of a preservation environment information output device that is applied to the case of performing the above-described adjustment. The example of the operation will be described below with reference to FIG. 24.

The sample setting unit 19 on which the fish 9 is set is positioned between the two image-taking member mount boards 24 (processing step S101), and left and right eyes of the fish 9 are irradiated with ultraviolet rays emitted from the ultraviolet sources 10a and 10b in the preservation environment information output device (processing step S102). The fish eyes may be irradiated with visible lights emitted from the visible light LEDs 25 instead of emitting the ultraviolet rays. If the left and right fish eyes are not located within the analysis target regions (processing step S103), the image-taking position is adjusted (processing step S104). If the left and right fish eyes are each located within the analysis target region, the preservation environment information output device irradiates the fish eyes with the ultraviolet rays of specific intensity emitted from the ultraviolet sources 10a and 10b (processing step S105), and takes a left eye image and a right eye image (processing step S106). Then, the preservation environment information output device discriminates the iris portion and the crystalline lens portion in each of the left eye image and the right eye image by the computer 14 (processing step S107), and calculates an average luminance value of the crystalline lens portion (processing step S108). If a bilateral difference in the average luminance value of the crystalline lens portion is not less than a specific value (e.g., 10) (namely, if the bilateral difference exceeds a range of small difference) (processing step S109), the intensity of the ultraviolet rays is adjusted (processing step S110), and the control flow is returned to the processing step S106 again. The adjustment of the intensity of the ultraviolet rays is performed, for example, by the computer 14 controlling, e.g., an irradiation controller that can change a current supplied to each ultraviolet LED, thus increasing or decreasing the intensity of the ultraviolet rays at one of the left and right sides or the intensities of the ultraviolet rays at both the left and right sides. If the bilateral difference in the average luminance value of the crystalline lens portion is less than the specific value (e.g., 10), an average luminance value of the iris portion of each fish eye is calculated (processing step S111), and the preservation environment of the fish is determined in accordance with the information 8 for determination (see FIG. 23) based on the bilateral difference in the average luminance value of the iris portion (processing step S112). Then, the preservation environment information output device displays a determination result on the display 15 (processing step S113).

Figure 25:
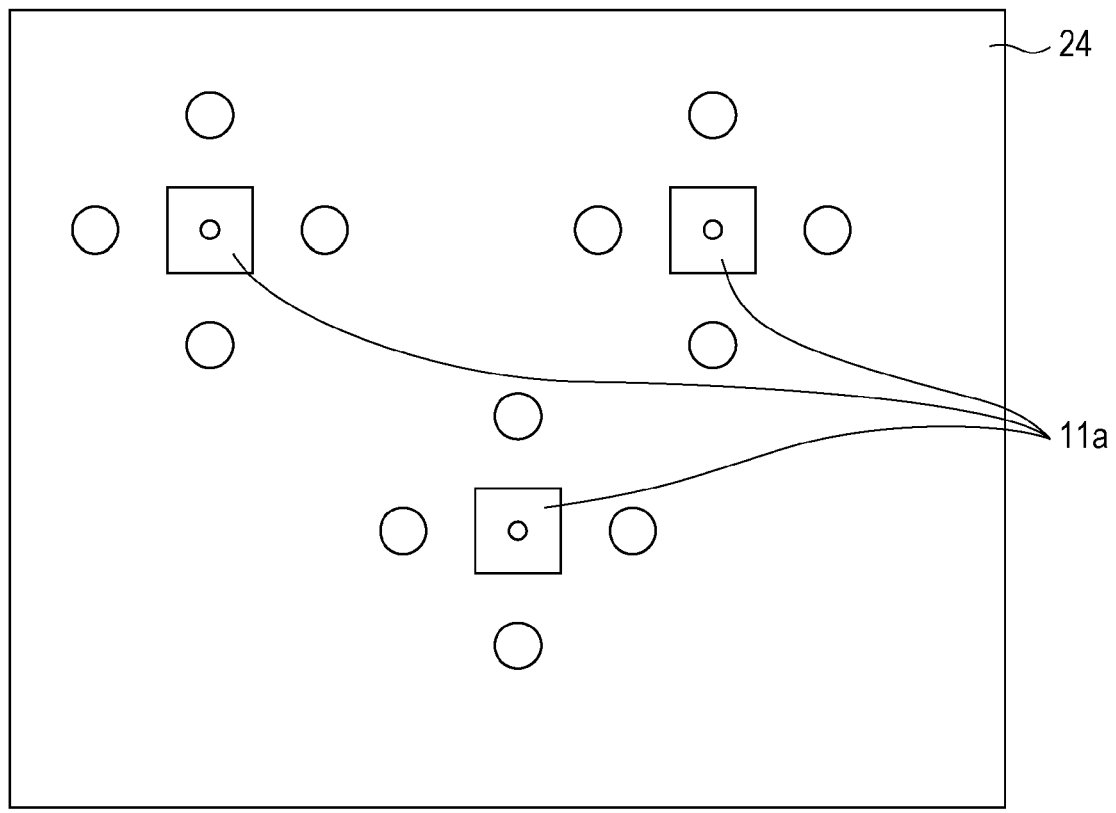
FIG. 25 illustrates an example in which a plurality of ultraviolet cameras is arranged on an image-taking member mount board.
Figure 26:
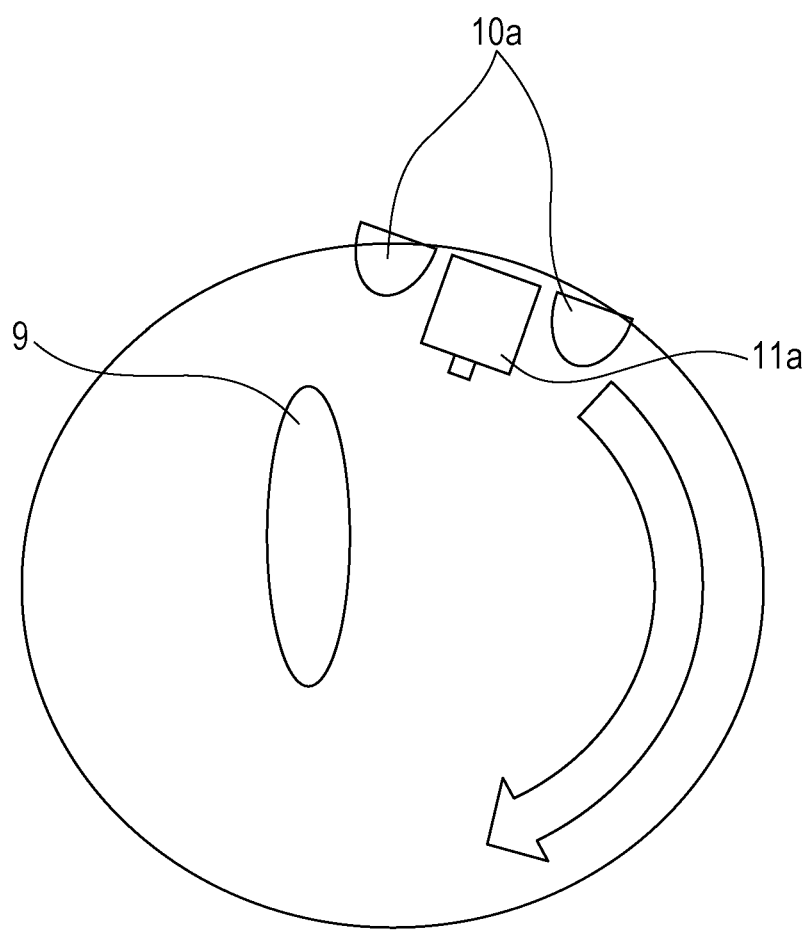
FIG. 26 illustrates an example in which an ultraviolet camera is moved around a fish.

Instead of moving the image-taking position (i.e., the fish or the ultraviolet camera) to take the image of the fish eye by the ultraviolet camera, a plurality of ultraviolet cameras 11a may be arranged on the image-taking member mount board 24, as illustrated in FIG. 25, such that any of the ultraviolet cameras 11a is able to take the image of the fish eye when the fish is set on the sample setting unit 19. Furthermore, as illustrated in FIG. 26, images may be taken plural times while the ultraviolet camera 11a is moved around the fish, to thereby obtain left and right eye images including the left fish eye and the right fish eye, respectively.

In addition, a polarization filter may be utilized to reduce a distortion of the taken image, which may be caused due to, e.g., halation in taking the image of the fish eye.

While the first embodiment has been described in connection with an example of comparing the freshness index values A at the left and right sides of the fish body, i.e., an example of determining the preservation environment based on a discrepancy in the freshness index value A between the left and right sides, the preservation environment may be determined depending on a discrepancy (including a difference and a ratio) in the luminance value of the iris portion between the left and right sides instead of the discrepancy in the freshness index value A between the left and right sides.

While each of the above-described embodiments employs the average luminance value of the iris portion and the average luminance value of the crystalline lens portion as the basis for calculating the freshness index value, the average luminance value is not limited to an exact average value in some cases. A luminance value representing the luminance of the iris portion and a luminance value representing the luminance of the crystalline lens portion may be used as the basis for calculating the freshness index value.

While the above-described embodiments have been described in connection with an example of implementing output of the information indicating the determination result of the preservation environment of the fish by displaying the information on the display 15, the information may be displayed on a screen, which is projected by a projector, instead of being displayed on the display 15. Alternatively, the output of the information indicating the determination result of the preservation environment of the fish may be implemented with methods other than displaying, for example, by printing the information, by generating voices speaking the information, or by transmitting the information to another device.

The whole or a part of the above-described processing procedures (e.g., the processing steps illustrated in FIG. 4 or 24) may be executed by employing just mechanisms and circuits of various devices (i.e., hardware), or by employing software. The execution of processing using software is implemented by an in-device processor executing control programs that are stored in a memory. The control programs may be distributed or circulated in the form recorded on a recording medium. For example, by installing the distributed control programs into a device and operating a processor in the device to execute the installed control programs, the device can operate to execute the processing procedures (e.g., the processing steps illustrated in FIG. 4 or 24).

While, in the above-described embodiments, the preservation environment information output devices are each mainly constituted by one computer 14, the preservation environment information output device may be constituted by plural units of equipment (including a device, a computer, etc.). The plural units of equipment can implement the function of determining the preservation environment of the fish through cooperation by communicating with one another.

Figure 27:
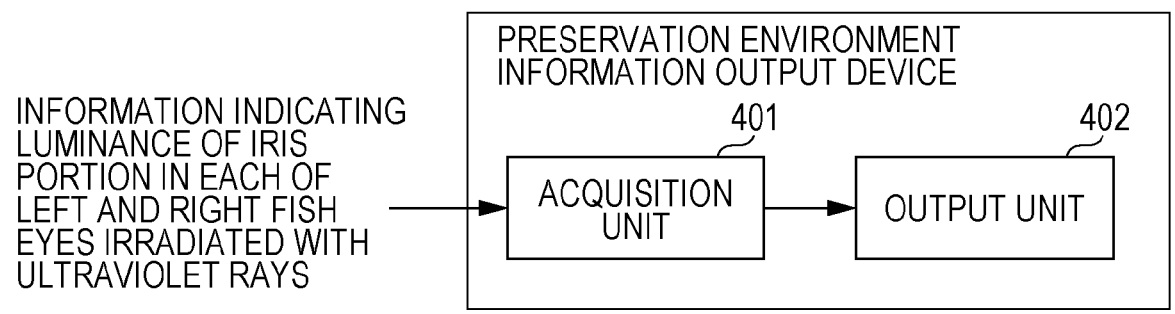
FIG. 27 is a functional block diagram of a preservation environment information output device according to another embodiment.

As illustrated in FIG. 27, a preservation environment information output device may have a configuration including an acquisition unit 401 that obtains information indicating luminance of an iris portion in each of left and right fish eyes irradiated with ultraviolet rays, and an output unit 402 that outputs environment information representing preservation environment of the fish, which has been determined based on a discrepancy in the luminance of the iris portion between the left and right sides. The acquisition unit 401 and the output unit 402 are implemented with the above-described computer 14 (see FIG. 2), for example. When the function of the determination unit 2 (see FIG. 1) is divided, for example, into an input side of receiving the ultraviolet images (i.e., the left eye image and the right eye image) and an output side of outputting the determination result, the acquisition unit 401 corresponds to at least part of the input side, and the output unit 402 corresponds to at least a part of the output side. The output unit 402 may be implemented in the form including the display 15 (see FIG. 2).

The information indicating luminance is an index indicating brightness of an image per unit area. The luminance value may be given, for example, as a value (e.g., a candela value) that is provided by measuring an obtained image with a luminance meter, or as a value that is provided by information expressing brightness per pixel of image data in 8-bit or 16-bit gradations. In the case of a color image, a value corresponding to each of respective gradations of RGB may be handled as the luminance value, or a value resulting from weighting respective luminance values of RGB and summing the weighted values may be handed as the luminance value. Moreover, while the luminance value is expressed in 8-bit gradations in the above description, it may be replaced with a value expressed in gradations with one of other bits than 8 bit, or replaced with a luminance value measured by a luminance meter.

A method of specifying a crystalline lens portion and an iris portion from an ultraviolet image may include (a) a step of detecting an edge region from the ultraviolet image, and (b) a step of detecting, from the edge region, a region that is analogous to a double-circle pattern. In this case, the double-circle pattern includes a first circle and a second circle having a larger radius than the first circle, a region inside the first circle involves the crystalline lens portion, and a region between a circular arc corresponding to the first circle and a circular arc corresponding to the second circle involves the iris portion. With the method described above, the crystalline lens portion and the iris portion can be individually specified from the ultraviolet image.

The crystalline lens portion and the iris portion may be individually specified from an infrared image in a similar manner to that described above.

The ultraviolet source may be a light source including wavelengths of an ultraviolet band (e.g., a wavelength band of 300 nm to 400 nm). The ultraviolet camera may take an image by receiving light of wavelengths in the above ultraviolet band.

The infrared source may be a light source including wavelengths of an infrared band (e.g., a wavelength band of 700 nm to 1000 nm). The infrared camera may take an image by receiving light of wavelengths in the above infrared band.

Various modifications of the above-described embodiments, which are conceivable by those skilled in the art, and various configurations resulting from optionally combining the components and the functions described in the different embodiments are also involved within the scope of the present disclosure.

The present disclosure can be utilized, in a delivery route of caught fresh fish up to consumer markets, to determine preservation environment of the fresh fish.

What is claimed is:

1. A preservation environment information output method comprising:
    emitting, using an ultraviolet light source, first ultraviolet rays;
    emitting, using the ultraviolet light source or a second ultraviolet light source, second ultraviolet rays;
    obtaining, using a hardware processor configured to execute the obtaining, first information indicating luminance of an iris portion of a left eye of a fish, the left eye being irradiated with the first ultraviolet rays, and second information indicating luminance of an iris portion of a right eye of the fish, the right eye being irradiated with the second ultraviolet rays; and
    outputting, using the hardware processor which is further configured to execute the outputting, environment information representing a preservation environment of the fish based on the first information and the second information.

2. The preservation environment information output method according to claim 1, further comprising:
    taking a first ultraviolet image containing an ultraviolet image of the left eye irradiated with the first ultraviolet rays and a second ultraviolet image containing an ultraviolet image of the right eye irradiated with the second ultraviolet rays,
    wherein the outputting comprises:
    determining the environment information; and
    outputting the environment information, and
    wherein the first information is extracted from the first ultraviolet image, and the second information is extracted from the second ultraviolet image.

3. The preservation environment information output method according to claim 2, further comprising:
    obtaining third information indicating luminance of a crystalline lens portion of the left eye, which is irradiated with the first ultraviolet rays, from the first ultraviolet image, and fourth information indicating luminance of a crystalline lens portion of the right eye, which is irradiated with the second ultraviolet rays, from the second ultraviolet image,
    wherein the determination of the environment information is performed by comparing a first freshness index value, which is obtained by normalizing the first information by employing the third information, with a second freshness index value, which is obtained by normalizing the second information by employing the fourth information.

4. The preservation environment information output method according to claim 2, further comprising:
    taking a first infrared image containing an infrared image of the left eye irradiated with first infrared rays and a second infrared image containing an infrared image of the right eye irradiated with second infrared rays; and
    obtaining fifth information indicating luminance of the iris portion of the left eye, which is irradiated with the first infrared rays, from the first infrared image, and sixth information indicating luminance of the iris portion of the right eye, which is irradiated with the second infrared rays, from the second infrared image, wherein the determination of the environment information is performed by comparing a third freshness index value, which is obtained by normalizing the first information by employing the fifth information, with a fourth freshness index value, which is obtained by normalizing the second information by employing the sixth information.

5. The preservation environment information output method according to claim 3, wherein when a discrepancy between the first freshness index value and the second freshness index value is smaller than a specific value, information indicating that temperatures at left and right sides of the fish have been held substantially equal is output as the environment information, and when the discrepancy is not smaller than the specific value, information indicating that the temperatures at the left and right sides of the fish have not been held substantially equal is output as the environment information.

6. The preservation environment information output method according to claim 5, wherein the environment information is output with inclusion of information indicating, based on the first information and the second information, whether the fish has been refrigerated at the left and right sides thereof.

7. The preservation environment information output method according to claim 4, wherein when a discrepancy between the third freshness index value and the fourth freshness index value is smaller than a specific value, information indicating that temperatures at left and right sides of the fish have been held substantially equal is output as the environment information, and when the discrepancy is not smaller than the specific value, information indicating that the temperatures at the left and right sides of the fish have not been held substantially equal is output as the environment information.

8. The preservation environment information output method according to claim 7, wherein the environment information is output with inclusion of information indicating, based on the first information and the second information, whether the fish has been refrigerated at the left and right sides thereof.

9. The preservation environment information output method according to claim 2, further comprising:
obtaining third information indicating luminance of a crystalline lens portion of the left eye, which is irradiated with the first ultraviolet rays, from the first ultraviolet image, and fourth information indicating luminance of a crystalline lens portion of the right eye, which is irradiated with the second ultraviolet rays, from the second ultraviolet image; and
when a discrepancy between the third information and the fourth information is not less than a specific value, the first ultraviolet image and the second ultraviolet image are taken again after adjusting one or both of intensities of the first ultraviolet rays and the second ultraviolet rays.

10. A preservation environment information output device comprising:
an acquisition unit that obtains first information indicating luminance of an iris portion of a left eye of a fish, the left eye being irradiated with first ultraviolet rays, and second information indicating luminance of an iris portion of a right eye of the fish, the right eye being irradiated with second ultraviolet rays; and
an output unit that outputs environment information representing a preservation environment of the fish based on the first information and the second information.

11. A non-transitory computer readable recording medium including a control program causing a device, which includes a processor, to execute preservation environment information output processing that determines preservation environment of a fish, the preservation environment information output processing comprising:
obtaining, using the processor which is configured to execute the obtaining, first information indicating luminance of an iris portion of a left eye of a fish, the left eye being irradiated with first ultraviolet rays emitted from an ultraviolet light source, and second information indicating luminance of an iris portion of a right eye of the fish, the right eye being irradiated with second ultraviolet rays emitted from the ultraviolet light source or a second ultraviolet light source; and
outputting, using the processor which is further configured to execute the outputting, environment information representing a preservation environment of the fish based on the first information and the second information.

\* \* \* \* \*